US005643714A

United States Patent [19]

Hadlock et al.

[11] Patent Number: 5,643,714

[45] Date of Patent: Jul. 1, 1997

[54] METHOD AND ASSAY FOR HTLV

[75] Inventors: Kenneth G. Hadlock, Hayward, Calif.; Chin-Joo Goh, Singapore, Singapore; Steven K.H. Foung, Stanford, Calif.

[73] Assignees: Genelabs Technologies, Inc., Redwood City; The Board of Trustees of the Leland Stanford Junior University, Stanford, both of Calif.

[21] Appl. No.: 14,153

[22] Filed: Feb. 5, 1993

Related U.S. Application Data

[63] Continuation-in-part of Ser. No. 653,091, Feb. 8, 1991, abandoned, which is a continuation-in-part of Ser. No. 366,313, Jun. 13, 1989, Pat. No. 5,066,579, which is a continuation of Ser. No. 948,270, Dec. 31, 1986, abandoned.

[51] Int. Cl.[6] .............................. C12Q 1/70; C12Q 1/68; G01N 33/53; C07K 14/15

[52] U.S. Cl. .................................. 435/5; 435/6; 435/7.1; 435/7.92; 530/324

[58] Field of Search .......................... 435/5, 6, 7.1, 7.92; 530/324

[56] References Cited

U.S. PATENT DOCUMENTS

| | | | |
|---|---|---|---|
| 4,446,122 | 5/1984 | Chu et al. | 435/7.23 |
| 4,588,681 | 5/1986 | Sawada et al. | 435/5 |
| 4,645,738 | 2/1987 | Knowles et al. | 435/7.23 |
| 4,661,445 | 4/1987 | Saxinger et al. | 435/5 |
| 4,663,436 | 5/1987 | Elder et al. | 530/324 |
| 4,689,398 | 8/1987 | Wu et al. | 530/327 |
| 4,722,888 | 2/1988 | Broder et al. | 435/5 |
| 4,724,258 | 2/1988 | Yoshida et al. | 530/350 |
| 4,731,326 | 3/1988 | Thompson et al. | 435/7.25 |
| 4,735,896 | 4/1988 | Wang et al. | 435/5 |
| 4,757,000 | 7/1988 | Tohmatsu et al. | 435/5 |
| 5,003,043 | 3/1991 | Akita et al. | 530/324 |
| 5,017,687 | 5/1991 | Vahlne et al. | 424/187.1 |
| 5,039,604 | 8/1991 | Papsidero | 435/5 |
| 5,066,579 | 11/1991 | Reyes | 435/7.1 |

FOREIGN PATENT DOCUMENTS

| | | |
|---|---|---|
| 0 113 078 | 7/1984 | European Pat. Off. . |
| 0 166 224 | 5/1985 | European Pat. Off. . |
| 0 214 555 | 8/1986 | European Pat. Off. . |
| 0 246 101 | 5/1987 | European Pat. Off. . |
| 0 267 622 | 11/1987 | European Pat. Off. . |
| 0 269 445 | 11/1987 | European Pat. Off. . |
| 0 345 792 | 12/1989 | European Pat. Off. . |
| 0 424 748 | 5/1991 | European Pat. Off. . |
| 2 122 343 | 4/1983 | United Kingdom . |
| 86/01834 | 3/1986 | WIPO . |
| 9015820 | 12/1990 | WIPO . |
| 91/07510 | 5/1991 | WIPO . |
| 91/07664 | 5/1991 | WIPO . |
| 92/13946 | 8/1992 | WIPO . |

OTHER PUBLICATIONS

Copeland et al., J. Immunol 137(9):2945–51.

Kurtu et al., J. Immunol 143(6):2024–2030. 1989.

Ehrlich et al, Virology 186(2):619–27. 1992.

Lipka et al, J. Infect Dis. 165(2):268–72. 1992.

Shah et al, Peptide Research 5(4):241–244. 1992.

Hoal et al, PNAS 88(13):5754–8. 1991.

Viscidi et al, J. Aqu. Imm. Def. Synd. 4(12):1190–8. 1991.

Blumberg et al, J. Aqu. Imm. Def. Synd. 5(3):294–302. 1992.

Palker et al, J. Immunol. 142(3):971–8. 1989.

Nakamura et al, J. Neuroimmunol 35(1–3):167–77. 1991.

Horal, P., et al., "Identification of type–specific linear epitopes in the glycoproteins gp46 and gp21 of human T–cell leukemia viruses type I and type II using synthetic peptides" *Proc. Nat. Acad. Sci. USA*, 88(13):5754–8 (1991).

Anderson, D.W., et al., "Serological Confirmation of Human T–Lymphotropic Virus Type I Infection in Healthy Blood and Plasma Donors," *Blood* 74(7): 2585–2591 (1989).

Blattner, W.A., et al., "The Human Type–C Retrovirus, HTLV, in Black From the Caribbean Region, and Relationship to Adult T–Cell Leukemia/Lymphoma," *Int. J. Cancer* 30: 257–264 (1982).

Blattner, W.A., et al., "Human T–Cell Leukemia–Lymphoma Virus and Adult T–Cell Leukemia," *JAMA* 250(8): 1074–1080 (1983).

Blayney, D.W., et al., "The Human T–Cell Leukemia–Lymphoma Virus in the Southeastern United States," *JAMA* 250(8): 1048–1052 (1983).

Catovsky, D., et al., "Adult T–Cell Lymphoma–Leukaemia in Blacks from the West Indies," *Lancet*, Apr. 20, 1982: 639–643 (1982).

Chen, Y–M.A., et al., "Antibody Reactivity to Different Regions of Human T–Cell Leukemia Virus Type 1 gp61 in Infected People," *J. Virology* 63(11): 4952–4957 (1989).

Chiba, J., et al., "Serodiagnosis of hepatitis C virus (HCV) infection with an HCV core protein molecularly expressed by a recombinant baculovirus," *Proc. Natl. Acad. Sci. USA* 88: 4641–4645 (1991).

Cainciolo, G.J., et al., "Inhibition of Lymphocyte Proliferation by a Synthetic Peptide Homologous to Retroviral Envelope Proteins," *Science* 230: 453–455 (1985).

Clapham, P., et al., "Pseudotypes of human T–cell leukemia virus types 1 and 2: Neutralization by patients' sera," *Proc. Natl. Acad. Sci. USA* 81: 2886–2889 (1984).

Essex, M., et al., "Antibodies to Human T–Cell Leukemia Virus Membrane Antigens (HTLV–MA) in Hemophiliacs," *Science* (Sep.): 1061–1064 (1983).

(List continued on next page.)

*Primary Examiner*—Michael P. Woodward

*Attorney, Agent, or Firm*—Charles K. Sholtz; Gary R. Fabian; Peter J. Dehlinger

[57] ABSTRACT

Novel HTLV-I and HTLV-II peptides are disclosed for use in diagnostic assays for detecting and confirming HTLV-I and HTLV-II infection in human sera. The peptides are derived from analogous regions of HTLV-I and HTLV-II gp21 envelope protein, and are diagnostic of HTLV-I or HTLV-II infection. The invention also includes an assay kit and method for detecting, and discriminating between, HTLV-I and HTLV-II infection in humans.

17 Claims, 16 Drawing Sheets

OTHER PUBLICATIONS

Gallo, R.C., et al., "Human T–cell leukemia–lymphoma virus (HTLV) is in T but not B lymphocytes from a patient with cutaneous T–cell lymphoma," *Proc. Natl. Acad. Sci. USA* 79: 5680–5683 (1982).

Gallo, R.C., et al., "Association of the Human Type C Retrovirus with a Subset of Adult T–Cell Cancers," *Cancer Res.* 43: 3892–3899 (1983).

Halbert, S.P., et al., "Quantitative Estimation by a Standardized Enzyme–Linked Immunosorbent Assay of Human T–Cell Lymphotropic Virus Type I Antibodies in Adult T–Cell Leukemia and Acquired Immune Deficiency Syndrome," *J. Clin. Microbiol.* 23(2): 212–216 (1986).

Hattori, S., et al., "Identification of gag and env Gene Products of Human T–Cell Leukemia Virus (HTLV)," *Virology* 136: 338–347 (1984).

Itamura, S., et al., "Expression of the gag gene of human T–cell leukemia virus type I in *Escherichia coli* and its diagnostic use," *Gene* 38: 57–64 (1985).

Iwatsuki, K., et al., "Production of Monoclonal Antibodies to Human T–cell Lymphotropic Virus Type 1 (HTLV–1) and Studies of Their Specificity," *Jpn. J. Dermatol.* 99: 1059–1065 (1989).

Kiyokawa, T., et al., "Envelope proteins of human T–cell leukemia virus: Expression in *Escherichia coli* and its application to studies of env gene functions," *Proc. Natl. Acad. Sci. USA* 81: 6202–6206 (1984).

Kline, R.L., et al., "Evaluation of enzyme immunoassays for antibody to human T–lymphotropic viruses type I/II," *Lancet* 337: 30–33 (1991).

Lal, R.B., et al., "Serologic Discrimination of Human T Cell Lymphotropic Virus Infection by Using a Synthetic Peptide–Based Enzyme Immunoassay," *J. Infect. Dis.* 163: 41–46 (1991).

Lee, T.H., et al., "Human T–cell leukemia virus–associated membrane antigens: Identity of the major antigens recognized after virus infection," *Proc. Natl. Acad. Sci. USA* 81: 3856–3860 (1984).

Lillehoj, E.P., et al., "Development and Evaluation of a Human T–Cell Leukemia Virus Type I Serologic Confirmatory Assay Incorporation a Recombinant Envelope Polypeptide," *J. Clin. Microbiol.* 28(12): 2653–2658 (1990).

Matsushita, S,. et al., "Human monoclonal antibody directed against an envelope glycoprotein of human T–cell leukemia virus type I," *Proc. Natl. Acad. Sci. USA* 83: 2672–2676 (1986).

Newman, M.J., et al., "Serological Characterization of Human T–Cell Leukemia (Lymphotropic) Virus, Type I (HTLV–I) Small Envelope Protein," *Virology* 150: 106–116 (1986).

Nyunoya, H., et al., "Expression of HTLV–I Envelope Protein Fused to Hydrophobic Amino–Terminal Peptide of Baculovirus Polyhedrin in Insect Cells and its Application for Serological Assays," *AIDS Res. H. Retroviruses* 6(11): 1311–1321 (1990).

Oroszlan, S., and T.D. Copeland, "Primary Structure and Processing of gag and env Gene Products of Human T–Cell Leukemia Viruses HTLV–$I_{CR}$ and HTLV–$I_{ATK}$," *Current Topics in Microbiol. and Immunol.* 115: 221–233 (1985).

Palker, T.J., et al. "Mapping of Immunogenic Regions of Human T Cell Leukemia Virus Type I (HTLV–I) gp46 and gp21 Envelope Glycoproteins with Env–Encoded Synthetic Peptides and a Monoclonal Antibody to gp46," *J. Immunol.* 142: 971–978 (1989).

Patarca, R., and W.A. Haseltine, "Sequence similarity among retroviruses—erratum," *Nature* 309: 728 (1984).

Poiesz, B.J., et al., "Detection and isolation of type C retrovirus particles from fresh and cultured lymphocytes of a patient with cutaneous T–cell lymphoma," *Proc. Natl. Acad. Sci. USA* 77: 7415–7419 (1980).

Poiesz, B.J., et al., "Isolation of a new type C retrovirus (HTLV) in primary uncultured cells of a patient with Sezary T–cell leukaemia," *Nature* 294: 268–271 (1981).

Ralston, S., et al., "Identification and Synthesis of the Epitope for a Human Monoclonal Antibody Which Can Neutralize Human T–cell Leukemia/Lymphotropic Virus Type I," *J. Biol. Chem.* 264(28): 16343–16346 (1989).

Robert–Guroff, M., et al., "Detection of the Human T Cell Lymphoma Virus p19 in Cells of Some Patients With Cutaneous T Cell Lymphoma and Leukemia Using a Monoclonal Antibody," *J. Exper. Med.* 154: 1957–1964 (1981).

Robert–Guroff, M., et al., "Evidence for Human T Cell Lymphoma–Leukemia Virus Infection of Family Members of Human T Cell Lymphoma–Leukemia Virus Positive T Cell Leukemia–Lymphoma Patients," *J. Exper. Med.* 157: 248–258 (1983).

Robert–Guroff, M., and E. Shepard, "A Monoclonal Antibody Specific for a 52,000–Molecular–Weight Human T–Cell Leukemia Virus–Associated Glycoprotein Expressed by Infected Cells," *J. Virology* 53(1): 214–220 (1985).

Samuel, K.P., et al., "Diagnostic Potential for Human Malignancies of Bacterially Produced HTLV–I Envelope Protein," *Science* 236: 1094–1097 (1984).

Saxinger, W., et al., "Human T–Cell Leukemia Virus (HTLV–I) Antibodies in Africa," *Science* (Sep. 28): 1473–1476 (1984).

Schupbach, J., et al., "Antigens on HTLV–Infected Cells Recognized by Leukemia and AIDS Sera Are Related to HTLV Viral Glycoprotein," *Science* 224: 607–610 (1984).

Seiki, M., et al., "Human adult T–cell leukemia virus: Complete nucleotide sequence of the provirus genome integrated in leukemia cell DNA," *Proc. Natl. Acad. Sci. USA* 80: 3618=2622 (1983).

Shimoyama, M., et al., "Anti–ATLA (Antibody to the Adult T–Cell Leukemia Cell–Associated Antigen)–Positive Hematologic Malignancies in the Kanto District," *Jpn. J. Clin. Oncol.* 12(1): 109–116 (1982).

Slamon, D.J., et al., "55. Identification of the Putative Transforming Protein of the Human T–Cell Leukemia Viruses HTLV–I and HTLV–II," *Report,* 5 Oct.: 291–299 (1984).

Sodroski, J., et al., "44. Sequence of the Envelope Glycoprotein Gene of Type II Human T Lymphotropic Virus," *Report,* 27 Jul.: 241–245 (1984).

Sugamura, K., et al., "Identification of a Glycoprotein, gp21, of Adult T Cell Leukemia Virus by Monoclonal Antibody," *J. Immun.* 132(6): 3180–3184 (1984).

Tanaka, Y., et al., "A Glycoprotein Antigen Detected with New Monoclonal Antibodies on the Surface of Human Lymphocytes Infected with Human T–Cell Leukemia Virus Type–I (HTLV–I)," *Int. J. Cancer* 36(5): 549–555 (1985).

Tanaka, Y., et al., "Generation and Characterization of Monoclonal Antibodies Against Multiple Epitopes on the C–Terminal Half of Envelope gp46 of Human T–Cell Leukemia Virus Type–I (HTLV–I)," *Int. J. Cancer* 46: 675–681 (1990).

Wang, J.J.G., et al., "Detection of antibodies to human T-lymphotropic virus type III by using a synthetic peptide of 21 amino acid residues corresponding to a highly antigenic segment of gp41 envelope protein," *Proc. Natl. Acad. Sci. USA* 83: 6159–6163 (1986).

Williams, A.E., et al., "Seroprevalence and Epidemiological Correlates of HTLV-I Infection in U.S. Blood Donors," *Science* 240: 643–646 (1988).

Williams, A.E., et al., "Human T-Lymphotropic Virus Type I Screening in Volunteer Blood Donors—United States, 1989," *MMWR* 39(50): 915–924 (1990).

Yoshida, M., et al., "Isolation and characterization of retrovirus from cell lines of human adult T-cell leukemia and its implication in the disease," *Proc. Natl. Acad. Sci. USA* 79: 2031–2035 (1982).

Fig. 2A

```
                                  Start of p21E (BamH I site)
                                  |-->
              Start 1A1B          |  End of gp46--| |- Start of gp21
              S  L  S  P  V  P  T  L  G  S  R  S  R  R   A  V
                 *        *        *        *
                6081      6091     6101     6111
             TCCTTGTCACCTGTTCCCACCCTAGGATCCCGCTCCCGCCGA GCGG
             |-1A->                G^GATCC(BamHI)

  P  V  A  V  W  L  V  S  A  L  A  M  G  A  G  V  A  G  G  I
*        *        *        *        *        *
6121     6131     6141     6151     6161     6171
TACCGGTGGCGGTCTGGCTTGTCTCCGCCCTGGCCATGGGAGCCGGAGTGGCTGGCGGGA
 <-1B-|     |-2A->

  T  G  S  M  S  L  A  S  G  K  S  L  L  H  E  V  D  K  D  I
*        *        *        *        *        *
6181     6191     6201     6211     6221     6231
TTACCGGCTCCATGTCCCTCGCCTCAGGAAAGAGCCTCCTACATGAGGTGGACAAAGATA

  S  Q  L  T  Q  A  I  V  K  N  H  K  N  L  L  K  I  A  Q  Y
*        *        *        *        *        *
6241     6251     6261     6271     6281     6291
TTTCCCAGTTAACTCAAGCAATAGTCAAAAACCACAAAAATCTACTCAAAATTGCGCAGT
                  |-MF1->  <-2B-|
```

```
   A  A  Q  N  R  R  G  L  D  L  L  F  W  E  Q  G  G  L  C  K
*         *         *         *         *         *
6301      6311      6321      6331      6341      6351
ATGCTGCCCAGAACAGACGAGGCCTTGATCTCCTGTTCTGGGAGCAAGGAGGATTATGCA
                              |-MF2->
                             <-MR2-|

   A  L  Q  E  Q  C  R  F  P  N  I  T  N  S  H  V  P  I  L  Q
*         *         *         *         *         *
6361      6371      6381      6391      6401      6411
AAGCATTACAAGAACAGTGCCGTTTTCCGAATATTACCAATTCCCATGTCCCAATACTAC
      |-3A->              <-MR1-|

   E  R  P  P  L  E  N  R  V  L  T  G  W  G  L  N  W  D  L  G
*         *         *         *         *         *
6421      6431      6441      6451      6461      6471
AAGAAAGACCCCCCCTTGAGAATCGAGTCCTGACTGGCTGGGGCCTTAACTGGGACCTTG
                                             <-3B-|

        End of p21E
           <--|
   L  S  Q  W  A  R
*         *
6481      6491
GCCTCTCACAGTGGGCTCGAG
           C^TCGAG(Xho I)
```

Fig. 2A (con't)

```
                                      p21E
                                     |-->
  S  L  A  P  V  P  P  P  A  T  R  R  R  R  A  V  P  I  A  V
*         *         *         *         *         *
6061      6071      6081      6091      6101      6111
TTCCCTCGCTCCCGTACCTCCTCCGGCGACAAGACGCCGCCGTGCCGTTCCAATAGCAGT

  W  L  V  S  A  L  A  A  G  T  G  I  A  G  G  V  T  G  S  L
*         *         *         *         *         *
6121      6131      6141      6151      6161      6171
GTGGCTTGTCTCCGCCCTAGCGGCCGGAACAGGTATCGCTGGTGGAGTAACAGGCTCCCT

  S  L  A  S  S  K  S  L  L  L  E  V  D  K  D  I  S  H  L  T
*         *         *         *         *         *
6181      6191      6201      6211      6221      6231
ATCTCTGGCTTCCAGTAAAAGCCTTCTCCTCGAGGTTGACAAAGACATCTCCCACCTTAC

  Q  A  I  V  K  N  H  Q  N  I  L  R  V  A  Q  Y  A  A  Q  N
*         *         *         *         *         *
6241      6251      6261      6271      6281      6291
CCAGGCCATAGTCAAAAATCATCAAAACATCCTCCGGGTTGCACAGTATGCAGCCCAAAA

  R  R  G  L  D  L  L  F  W  E  Q  G  G  L  C  K  A  I  Q  E
*         *         *         *         *         *
6301      6311      6321      6331      6341      6351
TAGACGAGGATTAGACCTCCTATTCTGGGAACAAGGGGGTTTGTGCAAGGCCATACAGGA
```

Fig. 2B

```
  Q   C   C   F   L   N   I   S   N   T   H   V   S   V   L   Q   E   R   P   P
*             *             *             *             *             *
6361          6371          6381          6391          6401          6411
GCAATGTTGCTTCCTCAACATCAGTAACACTCATGTATCCGTCCTCCAGGAACGGCCCCC

  L   E   K   R   V   I   T   G   W   G   L   N   W   D   L   G   L   S   Q   W
*             *             *             *             *             *
6421          6431          6441          6451          6461          6471
TCTTGAAAAACGTGTCATCACCGGCTGGGACTAAACTGGATCTTGGACTGTCCCAATG

    End of p21E
   <--|
  A   R   E   A   L   Q   T   G   I   T   I   L   A   L   L   L   L   V   I   L
*             *             *             *             *             *
6481          6491          6501          6511          6521          6531
GGCACGAGAAGCCCTCCAGACAGGCATAACCATTCTCGCTCTACTCCTCCTCGTCATATT
```

Fig. 2B (con't)

1A.> TCC GAA TTC TCC ATG GGT TCC TTG TCA CCT GTT CCC ACC

2A.> TCC GAA TTC GGA TCC TGG CTT GTC TCC GCC CTG GCC

MF1.> GC GAA TTC GGA TCC ATA GTC AAA AAC CAC AAA AAT C

MF2.> CC GAA TTC GGA TCC CTCCTGTTCTGGGAGCAAGG

3A.> TCC GAA TTC ACT AGT GGA TCC CAA GAA CAG TGC CGT TTT CCG

Fig. 3A

1B.> ACC ACT AGT ACC ACC ACC ACC GAATTC CAC CGG TAC CGC TCG GCG GGA

2B.> TGG GAA TTC GTG GTT TTT GAC TAT TGC TTG

MR1.> CGC GAA TTC G GA AAA CGG CAC TGT TC

MR2.> CGCGAATTCC AGGAGATCAA GGCCTCGTCT G

3B.> TGG GAA TTC GTT AAG GCC CCA GCC AGT CAG

Fig. 3B

```
   P  P  K  S  D  L  V  P  R  G  S  M  G  G  S  E  F  I  V  T  D  Z
*         *         *         *         *         *         *
901       911       921       931       941       951       961
ATCCTCCAAAATCGGATCTGGTTCCGCGTGGTTCCATGGGTGGATCCGAATTCATCGTGACTGACTGA
                                                  C^CATGG(NcoI) G^AATTC(EcoR1)
                                          G^GATCC(BamHI)
```

Fig. 3C

```
                           *                        *                         *
                          310¦-- gp21 -->          330                       350
gp46/21    SLSPVPTLGSRSRRAVPVAVWLVSALAMGAGVAGGITGSMSLASGKSLLHEVDK
p21E               LGSRSRRAVPVAVWLVSALAMGAGVAGGITGSMSLASGKSLLHEVDK

1A1B       SLSPVPTLGSRSRRAVPV
2A3B                         WLVSALAMGAGVAGGITGSMSLASGKSLLHEVDK
2A2B                         WLVSALAMGAGVAGGITGSMSLASGKSLLHEVDK
2B3A
MF1R2
MF2R1
3A3B

                 *                        *                        *
                410                      430                      450
gp21        ITNSHVPILQERPPLENRVLTGWGLNWDLGLSQWAREALQTGITLVALLLLVI
p21E        ITNSHVPILQERPPLENRVLTGWGLNWDLGLSQWAR

2A3B        ITNSHVSILQERPPLENRVLTGWGLN
3A3B        ITNSHVSILQERPPLENRVLTGWGLN
```

Fig. 4

```
                            *                   *
                           370                 390
gp46/21   DISQLTQAIVKNHKNLLKIAQYAAQNRRGLDLLFWEQGGLCKALQEQCRFPN
p21E      DISQLTQAIVKNHKNLLKIAQYAAQNRRGLDLLFWEQGGLCKALQEQCRFPN

1A1B
2A3B      DISQLTQAIVKNHKNLLKIAQYAAQNRRGLDLLFWEQGGLCKALQEQCCFLN
2A2B      DISQLTQAIVKNH
2B3A              IVKNHKNLLKIAQYAAQNRRGLDLLFWEQGGLCKALQEQCRFPN
MF1R2             IVKNHKNLLKIAQYAAQNRRGLDLL
MF2R1                                    LLFWEQGGLCKALQEQCRFPN
3A3B                                                 QEQCRFPN

                       *                *
                      470              488
gp21      LAGPCILRQLRHLPSRVRYPHYSLIKPESSLZ
p21E

2A3B
3A3B
```

Fig. 4 (con't)

```
2B3A                   IVKNHKNLLKIAQYAAQNRRGLDLLFWEQGGLCKALQEQCRFPN
                       ::::: : :  :::::::::::::::::::::::: :::: : :
2B3AS     HEVDKDISQLTQAIVKNHKNLLKIAQYAAQNRRGLDLLFWEQGGLCKALQEQCRFPNITNSHV
                       ::::: : :  :::::::::::::::::::::::: :::: : :
2B3AM     HEVDKDISQLTQAIVKNHKNLLKIAQYAAQNRRGLDLLFWEQGGLCKALQEQCCFLNITNSHV
                       ::::: : :  :::::::::::::::::::::::: :::: : :
2B3A8     HEVDKDISQLTQAIVKNHKNLLKVAQYAAQNRRGLDLLFWEQGGLCKALQEQCCFLNITNSHV
                       ::::: : :  :::::::::::::::::::::::: :::: : :
2B3AMO        KDISHLTQAIVKNHQNILRVAQYAAQNRRGLDLLFWEQGGLCKAIQEQCCFLNISNTHVSVLQ


2B3AC                  IVKNHX1NX2LX3X4AQYAAQNRRGLDLLFWEQGGLCKAX5QEQCX6FX7N
                            K  L  K I                         L     R  P
                            Q  I  R V                         I     C  L
```

Fig. 5

```
                              10              20              30
3A3B       QEQCRFPNITNSHVSILQERPPLENRVLTGWGLN
           X::: :: ::    :: :::::::::  ::::::::X
3A3BS   EQGGLCKALQEQCRFPNITNSHVPILQERPPLENRVLTGWGLNWDLGLSQWAR
           X::: :: ::    :: :::::::::  ::::::::X
3A3BM   EQGGLCKALQEQCCFLNITNSHVSILQERPPLENRVLTGWGLNWDLGLSQWAR
           X::: :: ::    :: :::::::::  ::::::::X
3A3BCH  EQGGLCKALQEQCCFLNITNSHVSMLQERPPLENRVLTGWGLNWDLGLSQWAR
           X::: :: ::    :: :::::::::  ::::::::X
3A3BMO     LCKAIQEQCCFLNISNTHVSVLQERPPLEKRVITGWGLNWDLGLSQWAREALQ

3A3BC   QEQCX$_1$FX$_2$NIX$_3$NX$_4$HVX$_5$X$_6$LQERPPLEX$_7$RVX$_8$TGWGLN
             R  P  T  S  S  I            N       L
             C  L  S  T  P  M            K       I
                        V
```

Fig. 6

```
               10        20        30        40        50        60
2b3a.s CCATAGTCAAAAACCACAAAAATCTACTCAAAATTGCGCAGTATGCTGCCCAGAACAGAC
       X:::::::::::: ::  ::::  : :::    :::: :::::::: ::::: :: ::::
hivv2c CCATAGTCAAAAATCATCAAAACATCCTCCGGGTTGCACAGTATGCAGCCCAAAATAGAC
        6250      6260      6270      6280      6290      6300

               70        80        90       100       110       120
2b3a.s GAGGCCTTGATCTCCTGTTCTGGGAGCAAGGAGGATTATGCAAAGCATTACAAGAACAGT
       ::::  : :: ::::: ::::::::X::::: :: :: ::::: ::  :::: :: :: :
hivv2c GAGGATTAGACCTCCTATTCTGGGAACAAGGGGGTTTGTGCAAGGCCATACAGGAGCAAT
        6310      6320      6330      6340      6350      6360

          130
2b3a.s GCCGTTTTCCGAA
       :  : :: :  ::
hivv2c GTTGCTTCCTCAA
        6370
```

Fig. 7

```
              10        20        30        40        50        60
3a3b.s  CAAGAACAGTGCCGTTTTCCGAATATCACTAATTCCCATGTCTCAATACTACAGGAAAGA
        :: :: :: ::  : :: :  :: :::: :::  : ::::: ::  : :: X::::: :
hivv2c  CAGGAGCAATGTTGCTTCCTCAACATCAGTAACACTCATGTATCCGTCCTCCAGGAACGG
            6360      6370      6380      6390      6400      6410

              70        80        90       100
3a3b.s  CCCCCCCTTGAGAATCGAGTCCTGACTGGCTGGGGCCTTAAC
        ::::: ::::: :: :: ::: : :: :::::::X :: :::
hivv2c  CCCCCTCTTGAAAAACGTGTCATCACCGGCTGGGGACTAAAC
            6420      6430      6440      6450
```

Fig. 8

```
                        TAPPLLPHSNLDHILEPS                            K163

  gt-SLLVDAPGYDPIWFLNTEPSQLPPTAPPLLPHSNLDHILEPSIPWKSKLLTLVQL          MTA-5

  gt-SLLVDAPGYDPIWFLNTEPSQLPPTAPPLLPHSNLDHILEPSIPWKSK-gt              MTA-1
CGFPSSLLVDAPGYDPIWFLNTEPSQLPPTAPPLLPHSNLDHILEPS-gt                    MTA-4
CGFPFSLLVDAPGYDPIWFLNTEPSQLPPTAPPLLPHSNLDHILEPSIPWKSKLLTLVQL          HTLV-I
||    |||||||||| ||   || | ||| |||   | | | | ||  |  | |   ||
CGSSMTLLVDAPGYDPLWFITSEPTQPPPTSPPLVHDSDLEHVLTPSTSWTTKILKFIQL          HTLV-II
  gt-MTLLVDAPGYDPLWFITSEPTQPPPTSPPLVHDSDLEHVLTPSTSWTTK-gt             GH2-K15

                                SPPLVHDSDLEHVLTPSTSWTTKTK             K35
                                SPPLVHDSDLEHVLTPS                     K34
           DAPGYDPLWFITSEPTQPPPTSPPLVHDSDLEHVLTPSTSWTTK-gt            K55
```

```
                                          K163

TLQSTJYYCIVCIDRASLSTWHV-gt               MTA-5

                                          MTA-1
                                          MTA-4
TLQSTNYYCIVCIDRASLSTWHVLY-               HTLV-I
||||||| |  || || ||| |||||
TLQSTNYSCMVCVDRSSLSSWHVLY-               HTLV-II
                                          GH2-K15


                                          K35
                                          K34
                                          K55
```

Fig. 9 (con't)

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AC, Fig. 5

( i x ) FEATURE:
( A ) NAME/KEY: Modified-site
( B ) LOCATION: 6
( D ) OTHER INFORMATION: /note= "where Xaa is K or Q"

( i x ) FEATURE:
( A ) NAME/KEY: Modified-site
( B ) LOCATION: 8
( D ) OTHER INFORMATION: /note= "where Xaa is L or I"

( i x ) FEATURE:
( A ) NAME/KEY: Modified-site
( B ) LOCATION: 10
( D ) OTHER INFORMATION: /note= "where Xaa is K or R"

( i x ) FEATURE:
( A ) NAME/KEY: Modified-site
( B ) LOCATION: 11
( D ) OTHER INFORMATION: /note= "where Xaa is I or V"

( i x ) FEATURE:
( A ) NAME/KEY: Modified-site
( B ) LOCATION: 36
( D ) OTHER INFORMATION: /note= "where Xaa is L or I"

( i x ) FEATURE:
( A ) NAME/KEY: Modified-site
( B ) LOCATION: 41
( D ) OTHER INFORMATION: /note= "where Xaa is R or C"

( i x ) FEATURE:
( A ) NAME/KEY: Modified-site
( B ) LOCATION: 43
( D ) OTHER INFORMATION: /note= "where Xaa is P or L"

( x i ) SEQUENCE DESCRIPTION: SEQ ID NO:1:

```
Ile Val Lys Asn His Xaa Asn Xaa Leu Xaa Xaa Ala Gln Tyr Ala Ala
1               5                   10                  15

Gln Asn Arg Arg Gly Leu Asp Leu Leu Phe Trp Glu Gln Gly Gly Leu
            20                  25                  30

Cys Lys Ala Xaa Gln Glu Gln Cys Xaa Phe Xaa Asn
        35                  40
```

( 2 ) INFORMATION FOR SEQ ID NO:2:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BC, Fig. 6

( i x ) FEATURE:
( A ) NAME/KEY: Modified-site
( B ) LOCATION: 5
( D ) OTHER INFORMATION: /note= "where Xaa is R or C"

( i x ) FEATURE:
( A ) NAME/KEY: Modified-site
( B ) LOCATION: 7
( D ) OTHER INFORMATION: /note= "where Xaa is P or L"

( i x ) FEATURE:
( A ) NAME/KEY: Modified-site
( B ) LOCATION: 10
( D ) OTHER INFORMATION: /note= "where Xaa is T or S"

( i x ) FEATURE:
( A ) NAME/KEY: Modified-site
( B ) LOCATION: 12
( D ) OTHER INFORMATION: /note= "where Xaa is S or T"

( i x ) FEATURE:
( A ) NAME/KEY: Modified-site
( B ) LOCATION: 15
( D ) OTHER INFORMATION: /note= "where Xaa is S or P"

( i x ) FEATURE:
( A ) NAME/KEY: Modified-site
( B ) LOCATION: 16
( D ) OTHER INFORMATION: /note= "where Xaa is I, M or V"

( i x ) FEATURE:
( A ) NAME/KEY: Modified-site
( B ) LOCATION: 25
( D ) OTHER INFORMATION: /note= "where Xaa is N or K"

( i x ) FEATURE:
( A ) NAME/KEY: Modified-site
( B ) LOCATION: 28
( D ) OTHER INFORMATION: /note= "where Xaa is L or I"

( x i ) SEQUENCE DESCRIPTION: SEQ ID NO:2:

Gln Glu Gln Cys Xaa Phe Xaa Asn Ile Xaa Asn Xaa His Val Xaa Xaa
1 5 10 15

Leu Gln Glu Arg Pro Pro Leu Glu Xaa Arg Val Xaa Thr Gly Trp Gly
20 25 30

Leu Asn ( 2 ) INFORMATION FOR SEQ ID NO:3:

( i ) SEQUENCE CHARACTERISTICS:
( A ) LENGTH: 47 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: MTA-1, Fig. 9

( x i ) SEQUENCE DESCRIPTION: SEQ ID NO:3:

Leu Leu Val Asp Ala Pro Gly Tyr Asp Pro Ile Trp Phe Leu Asn Thr
1 5 10 15

Glu Pro Ser Gln Leu Pro Pro Thr Ala Pro Pro Leu Leu Pro His Ser
20 25 30

Asn Leu Asp His Ile Leu Glu Pro Ser Ile Pro Trp Lys Ser Lys
35 40 45

-continued ( 2 ) INFORMATION FOR SEQ ID NO:4:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: K55 or "4,"Fig. 9

( x i ) SEQUENCE DESCRIPTION: SEQ ID NO:4:

```
Asp Ala Pro Gly Tyr Asp Pro Leu Trp Phe Ile Thr Ser Glu Pro Thr
1               5                   10                  15

Gln Pro Pro Pro Thr Ser Pro Pro Leu Val His Asp Ser Asp Leu Glu
            20                  25                  30

His Val Leu Thr Pro Ser Thr Ser Trp Thr Thr Lys
        35                  40
```

( 2 ) INFORMATION FOR SEQ ID NO:5:

( i ) SEQUENCE CHARACTERISTICS:
( A ) LENGTH: 427 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: p21E(I)CS, Fig. 2A ( x i ) SEQUENCE DESCRIPTION: SEQ ID NO:5:

```
TCCTTGTCAC CTGTTCCCAC CCTAGGATCC CGCTCCCGCC GAGCGGTACC GGTGGCGGTC    60

TGGCTTGTCT CCGCCCTGGC CATGGGAGCC GGAGTGGCTG GCGGGATTAC CGGCTCCATG   120

TCCCTCGCCT CAGGAAAGAG CCTCCTACAT GAGGTGGACA AAGATATTTC CCAGTTAACT   180

CAAGCAATAG TCAAAAACCA CAAAAATCTA CTCAAAATTG CGCAGTATGC TGCCCAGAAC   240

AGACGAGGCC TTGATCTCCT GTTCTGGGAG CAAGGAGGAT TATGCAAAGC ATTACAAGAA   300

CAGTGCCGTT TTCCGAATAT TACCAATTCC CATGTCCCAA TACTACAAGA AAGACCCCCC   360

CTTGAGAATC GAGTCCTGAC TGGCTGGGGC CTTAACTGGG ACCTTGGCCT CTCACAGTGG   420

GCTCGAG                                                             427
```

( 2 ) INFORMATION FOR SEQ ID NO:6:

( i ) SEQUENCE CHARACTERISTICS:
( A ) LENGTH: 142 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: p21E(I), Fig. 2A ( x i ) SEQUENCE DESCRIPTION: SEQ ID NO:6:

```
Ser Leu Ser Pro Val Pro Thr Leu Gly Ser Arg Ser Arg Arg Ala Val
1               5                   10                  15

Pro Val Ala Val Trp Leu Val Ser Ala Leu Ala Met Gly Ala Gly Val
```

-continued 20 25 30

Ala Gly Gly Ile Thr Gly Ser Met Ser Leu Ala Ser Gly Lys Ser Leu
35 40 45

Leu His Glu Val Asp Lys Asp Ile Ser Gln Leu Thr Gln Ala Ile Val
50 55 60

Lys Asn His Lys Asn Leu Leu Lys Ile Ala Gln Tyr Ala Ala Gln Asn
65 70 75 80

Arg Arg Gly Leu Asp Leu Leu Phe Trp Glu Gln Gly Gly Leu Cys Lys
85 90 95

Ala Leu Gln Glu Gln Cys Arg Phe Pro Asn Ile Thr Asn Ser His Val
100 105 110

Pro Ile Leu Gln Glu Arg Pro Pro Leu Glu Asn Arg Val Leu Thr Gly
115 120 125

Trp Gly Leu Asn Trp Asp Leu Gly Leu Ser Gln Trp Ala Arg
130 135 140

( 2 ) INFORMATION FOR SEQ ID NO:7:

( i ) SEQUENCE CHARACTERISTICS:
( A ) LENGTH: 480 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: p21E(II)CS, Fig. 2B ( x i ) SEQUENCE DESCRIPTION: SEQ ID NO:7:

TTCCCTCGCT CCCGTACCTC CTCCGGCGAC AAGACGCCGC CGTGCCGTTC CAATAGCAGT 60

GTGGCTTGTC TCCGCCCTAG CGGCCGGAAC AGGTATCGCT GGTGGAGTAA CAGGCTCCCT 120

ATCTCTGGCT TCCAGTAAAA GCCTTCTCCT CGAGGTTGAC AAAGACATCT CCCACCTTAC 180

CCAGGCCATA GTCAAAAATC ATCAAAACAT CCTCCGGGTT GCACAGTATG CAGCCCAAAA 240

TAGACGAGGA TTAGACCTCC TATTCTGGGA ACAAGGGGGT TTGTGCAAGG CCATACAGGA 300

GCAATGTTGC TTCCTCAACA TCAGTAACAC TCATGTATCC GTCCTCCAGG AACGGCCCCC 360

TCTTGAAAAA CGTGTCATCA CCGGCTGGGG ACTAAACTGG GATCTTGGAC TGTCCCAATG 420

GGCACGAGAA GCCCTCCAGA CAGGCATAAC CATTCTCGCT CTACTCCTCC TCGTCATATT 480

( 2 ) INFORMATION FOR SEQ ID NO:8:

( i ) SEQUENCE CHARACTERISTICS:
( A ) LENGTH: 160 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: p21E(II), Fig. 2B ( x i ) SEQUENCE DESCRIPTION: SEQ ID NO:8:

Ser Leu Ala Pro Val Pro Pro Pro Ala Thr Arg Arg Arg Arg Ala Val
1 5 10 15

Pro Ile Ala Val Trp Leu Val Ser Ala Leu Ala Ala Gly Thr Gly Ile
20 25 30

-continued

| | | | | | | | | | | | | | | | |
|---|---|---|---|---|---|---|---|---|---|---|---|---|---|---|---|
| Ala | Gly | Gly 35 | Val | Thr | Gly | Ser | Leu 40 | Ser | Leu | Ala | Ser | Ser 45 | Lys | Ser | Leu |
| Leu | Leu 50 | Glu | Val | Asp | Lys | Asp 55 | Ile | Ser | His | Leu | Thr 60 | Gln | Ala | Ile | Val |
| Lys 65 | Asn | His | Gln | Asn | Ile 70 | Leu | Arg | Val | Ala | Gln 75 | Tyr | Ala | Ala | Gln | Asn 80 |
| Arg | Arg | Gly | Leu | Asp 85 | Leu | Leu | Phe | Trp | Glu 90 | Gln | Gly | Gly | Leu | Cys 95 | Lys |
| Ala | Ile | Gln | Glu 100 | Gln | Cys | Cys | Phe | Leu 105 | Asn | Ile | Ser | Asn | Thr 110 | His | Val |
| Ser | Val | Leu 115 | Gln | Glu | Arg | Pro | Pro 120 | Leu | Glu | Lys | Arg | Val 125 | Ile | Thr | Gly |
| Trp | Gly 130 | Leu | Asn | Trp | Asp | Leu 135 | Gly | Leu | Ser | Gln | Trp 140 | Ala | Arg | Glu | Ala |
| Leu 145 | Gln | Thr | Gly | Ile | Thr 150 | Ile | Leu | Ala | Leu | Leu 155 | Leu | Leu | Val | Ile | Leu 160 |

( 2 ) INFORMATION FOR SEQ ID NO:9:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: FP-1A, Fig. 3A ( x i ) SEQUENCE DESCRIPTION: SEQ ID NO:9:

TCCGAATTCT CCATGGGTTC CTTGTCACCT GTTCCCACC 39

( 2 ) INFORMATION FOR SEQ ID NO:10:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: FP-2A, Fig. 3A ( x i ) SEQUENCE DESCRIPTION: SEQ ID NO:10:

TCCGAATTCG GATCCTGGCT TGTCTCCGCC CTGGCC 36

( 2 ) INFORMATION FOR SEQ ID NO:11:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: FP-MF1, Fig. 3A

-continued ( x i ) SEQUENCE DESCRIPTION: SEQ ID NO:11:

GCGAATTCGG ATCCATAGTC AAAAACCACA AAAATC 36

( 2 ) INFORMATION FOR SEQ ID NO:12:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: MF2, Fig. 3A ( x i ) SEQUENCE DESCRIPTION: SEQ ID NO:12:

CCGAATTCGG ATCCCTCCTG TTCTGGGAGC AAGG 34

( 2 ) INFORMATION FOR SEQ ID NO:13:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: FP-3A, Fig. 3A ( x i ) SEQUENCE DESCRIPTION: SEQ ID NO:13:

TCCGAATTCA CTAGTGGATC CCAAGAACAG TGCCGTTTTC CG 42

( 2 ) INFORMATION FOR SEQ ID NO:14:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: RP-1B, Fig. 3B ( x i ) SEQUENCE DESCRIPTION: SEQ ID NO:14:

ACCACTAGTA CCACCACCAC CGAATTCCAC CGGTACCGCT CGGCGGGA 48

( 2 ) INFORMATION FOR SEQ ID NO:15:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: RP-2B, Fig. 3B

-continued ( x i ) SEQUENCE DESCRIPTION: SEQ ID NO:15:

TGGGAATTCG TGGTTTTTGA CTATTGCTTG 30

( 2 ) INFORMATION FOR SEQ ID NO:16:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: RP-MR1, Fig. 3B ( x i ) SEQUENCE DESCRIPTION: SEQ ID NO:16:

CGCGAATTCG GAAAACGGCA CTGTTC 26

( 2 ) INFORMATION FOR SEQ ID NO:17:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: MR2, Fig. 3B ( x i ) SEQUENCE DESCRIPTION: SEQ ID NO:17:

CGCGAATTCC AGGAGATCAA GGCCTCGTCT G 31

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: RP-3B, Fig. 3B ( x i ) SEQUENCE DESCRIPTION: SEQ ID NO:18:

TGGGAATTCG TTAAGGCCCC AGCCAGTCAG 30

( 2 ) INFORMATION FOR SEQ ID NO:19:

( i ) SEQUENCE CHARACTERISTICS:
( A ) LENGTH: 18 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 1A1B, Fig. 4

( x i ) SEQUENCE DESCRIPTION: SEQ ID NO:19:

-continued

Ser Leu Ser Pro Val Pro Thr Leu Gly Ser Arg Ser Arg Arg Ala Val
1 5 10 15

Pro Val ( 2 ) INFORMATION FOR SEQ ID NO:20:

( i ) SEQUENCE CHARACTERISTICS:
( A ) LENGTH: 47 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2A2B, Fig. 4

( x i ) SEQUENCE DESCRIPTION: SEQ ID NO:20:

Trp Leu Val Ser Ala Leu Ala Met Gly Ala Gly Val Ala Gly Gly Ile
1 5 10 15

Thr Gly Ser Met Ser Leu Ala Ser Gly Lys Ser Leu Leu His Glu Val
20 25 30

Asp Lys Asp Ile Ser Gln Leu Thr Gln Ala Ile Val Lys Asn His
35 40 45

( 2 ) INFORMATION FOR SEQ ID NO:21:

( i ) SEQUENCE CHARACTERISTICS:
( A ) LENGTH: 86 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2A3B, Fig. 4

( x i ) SEQUENCE DESCRIPTION: SEQ ID NO:21:

Trp Leu Val Ser Ala Leu Ala Met Gly Ala Gly Val Ala Gly Gly Ile
1 5 10 15

Thr Gly Ser Met Ser Leu Ala Ser Gly Lys Ser Leu Leu His Glu Val
20 25 30

Asp Lys Asp Ile Ser Gln Leu Thr Gln Ala Ile Val Lys Asn His Lys
35 40 45

Asn Leu Leu Lys Ile Ala Gln Tyr Ala Ala Gln Asn Arg Arg Gly Leu
50 55 60

Asp Leu Leu Phe Trp Glu Gln Gly Gly Leu Cys Lys Ala Leu Gln Glu
65 70 75 80

Gln Cys Cys Phe Leu Asn
85

( 2 ) INFORMATION FOR SEQ ID NO:22:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:

( C ) INDIVIDUAL ISOLATE: 2B3A, Fig. 5

( x i ) SEQUENCE DESCRIPTION: SEQ ID NO:22:

Ile Val Lys Asn His Lys Asn Leu Leu Lys Ile Ala Gln Tyr Ala Ala
1 5 10 15

Gln Asn Arg Arg Gly Leu Asp Leu Leu Phe Trp Glu Gln Gly Gly Leu
20 25 30

Cys Lys Ala Leu Gln Glu Gln Cys Arg Phe Pro Asn
35 40

( 2 ) INFORMATION FOR SEQ ID NO:23:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3B, Fig. 6

( x i ) SEQUENCE DESCRIPTION: SEQ ID NO:23:

Gln Glu Gln Cys Arg Phe Pro Asn Ile Thr Asn Ser His Val Ser Ile
1 5 10 15

Leu Gln Glu Arg Pro Pro Leu Glu Asn Arg Val Leu Thr Gly Trp Gly
20 25 30

Leu Asn ( 2 ) INFORMATION FOR SEQ ID NO:24:

( i ) SEQUENCE CHARACTERISTICS:
( A ) LENGTH: 25 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: MF1R2, Fig. 4

( x i ) SEQUENCE DESCRIPTION: SEQ ID NO:24:

Ile Val Lys Asn His Lys Asn Leu Leu Lys Ile Ala Gln Tyr Ala Ala
1 5 10 15

Gln Asn Arg Arg Gly Leu Asp Leu Leu
20 25

( 2 ) INFORMATION FOR SEQ ID NO:25:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: MF2R1, Fig. 4

( x i ) SEQUENCE DESCRIPTION: SEQ ID NO:25:

Leu Leu Phe Trp Glu Gln Gly Gly Leu Cys Lys Ala Leu Gln Glu Gln
1 5 10 15

Cys Arg Phe Pro Asn
20

( 2 ) INFORMATION FOR SEQ ID NO:26:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AS, Fig. 5

( x i ) SEQUENCE DESCRIPTION: SEQ ID NO:26:

Ile Val Lys Asn His Lys Asn Leu Leu Lys Ile Ala Gln Tyr Ala Ala
1 5 10 15

Gln Asn Arg Arg Gly Leu Asp Leu Leu Phe Trp Glu Gln Gly Gly Leu
20 25 30

Cys Lys Ala Leu Gln Glu Gln Cys Arg Phe Pro Asn
35 40

( 2 ) INFORMATION FOR SEQ ID NO:27:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AM, Fig. 5

( x i ) SEQUENCE DESCRIPTION: SEQ ID NO:27:

Ile Val Lys Asn His Lys Asn Leu Leu Lys Ile Ala Gln Tyr Ala Ala
1 5 10 15

Gln Asn Arg Arg Gly Leu Asp Leu Leu Phe Trp Glu Gln Gly Gly Leu
20 25 30

Cys Lys Ala Leu Gln Glu Gln Cys Cys Phe Leu Asn
35 40

( 2 ) INFORMATION FOR SEQ ID NO:28:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AB, Fig. 5

( x i ) SEQUENCE DESCRIPTION: SEQ ID NO:28:

Ile Val Lys Asn His Lys Asn Leu Leu Lys Val Ala Gln Tyr Ala Ala
1 5 10 15

Gln Asn Arg Arg Gly Leu Asp Leu Leu Phe Trp Glu Gln Gly Gly Leu
20 25 30

Cys Lys Ala Leu Gln Glu Gln Cys Cys Phe Leu Asn

-continued 35 40

( 2 ) INFORMATION FOR SEQ ID NO:29:

( i ) SEQUENCE CHARACTERISTICS:
( A ) LENGTH: 44 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AMO, Fig. 5

( x i ) SEQUENCE DESCRIPTION: SEQ ID NO:29:

Ile Val Lys Asn His Gln Asn Ile Leu Arg Val Ala Gln Tyr Ala Ala
1 5 10 15

Gln Asn Arg Arg Gly Leu Asp Leu Leu Phe Trp Glu Gln Gly Gly Leu
20 25 30

Cys Lys Ala Ile Gln Glu Gln Cys Cys Phe Leu Asn
35 40

( 2 ) INFORMATION FOR SEQ ID NO:30:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3B, Fig. 4

( x i ) SEQUENCE DESCRIPTION: SEQ ID NO:30:

Gln Glu Gln Cys Arg Phe Pro Asn Ile Thr Asn Ser His Val Ser Ile
1 5 10 15

Leu Gln Glu Arg Pro Pro Leu Glu Asn Arg Val Leu Thr Gly Trp Gly
20 25 30

Leu Asn ( 2 ) INFORMATION FOR SEQ ID NO:31:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BS, Fig. 6

( x i ) SEQUENCE DESCRIPTION: SEQ ID NO:31:

Gln Glu Gln Cys Arg Phe Pro Asn Ile Thr Asn Ser His Val Pro Ile
1 5 10 15

Leu Gln Glu Arg Pro Pro Leu Glu Asn Arg Val Leu Thr Gly Trp Gly
20 25 30

Leu Asn ( 2 ) INFORMATION FOR SEQ ID NO:32:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BM, Fig. 6

( x i ) SEQUENCE DESCRIPTION: SEQ ID NO:32:

Gln Glu Gln Cys Cys Phe Leu Asn Ile Thr Asn Ser His Val Ser Ile
1 5 10 15

Leu Gln Glu Arg Pro Pro Leu Glu Asn Arg Val Leu Thr Gly Trp Gly
20 25 30

Leu Asn ( 2 ) INFORMATION FOR SEQ ID NO:33:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BCH, Fig. 6

( x i ) SEQUENCE DESCRIPTION: SEQ ID NO:33:

Gln Glu Gln Cys Cys Phe Leu Asn Ile Thr Asn Ser His Val Ser Met
1 5 10 15

Leu Gln Glu Arg Pro Pro Leu Glu Asn Arg Val Leu Thr Gly Trp Gly
20 25 30

Leu Asn ( 2 ) INFORMATION FOR SEQ ID NO:34:

( i ) SEQUENCE CHARACTERISTICS:
( A ) LENGTH: 34 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BMO, Fig. 6

( x i ) SEQUENCE DESCRIPTION: SEQ ID NO:34:

Gln Glu Gln Cys Cys Phe Leu Asn Ile Ser Asn Thr His Val Ser Val
1 5 10 15

Leu Gln Glu Arg Pro Pro Leu Glu Lys Arg Val Ile Thr Gly Trp Gly
20 25 30

Leu Asn ( 2 ) INFORMATION FOR SEQ ID NO:35:

( i ) SEQUENCE CHARACTERISTICS:
( A ) LENGTH: 133 base pairs
( B ) TYPE: nucleic acid
( C ) STRANDEDNESS: double -continued ( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: 2B3A(I), Fig. 7

( x i ) SEQUENCE DESCRIPTION: SEQ ID NO:35:

CCATAGTCAA AAACCACAAA AATCTACTCA AAATTGCGCA GTATGCTGCC CAGAACAGAC 60

GAGGCCTTGA TCTCCTGTTC TGGGAGCAAG GAGGATTATG CAAAGCATTA CAAGAACAGT 120

GCCGTTTTCC GAA 133

( 2 ) INFORMATION FOR SEQ ID NO:36:

( i ) SEQUENCE CHARACTERISTICS:
( A ) LENGTH: 133 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: 2B3A(II), Fig. 7

( x i ) SEQUENCE DESCRIPTION: SEQ ID NO:36:

CCATAGTCAA AAATCATCAA AACATCCTCC GGGTTGCACA GTATGCAGCC CAAAATAGAC 60

GAGGATTAGA CCTCCTATTC TGGGAACAAG GGGGTTTGTG CAAGGCCATA CAGGAGCAAT 120

GTTGCTTCCT CAA 133

( 2 ) INFORMATION FOR SEQ ID NO:37:

( i ) SEQUENCE CHARACTERISTICS:
( A ) LENGTH: 102 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: 3A3B(I), Fig. 8

( x i ) SEQUENCE DESCRIPTION: SEQ ID NO:37:

CAAGAACAGT GCCGTTTTCC GAATATCACT AATTCCCATG TCTCAATACT ACAGGAAAGA 60

CCCCCCCTTG AGAATCGAGT CCTGACTGGC TGGGGCCTTA AC 102

( 2 ) INFORMATION FOR SEQ ID NO:38:

( i ) SEQUENCE CHARACTERISTICS:
( A ) LENGTH: 102 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: 3A3B(II), Fig. 8

( x i ) SEQUENCE DESCRIPTION: SEQ ID NO:38:

-continued

```
CAGGAGCAAT GTTGCTTCCT CAACATCAGT AACACTCATG TATCCGTCCT CCAGGAACGG        60

CCCCCTCTTG AAAAACGTGT CATCACCGGC TGGGGACTAA AC                          102
```

( 2 ) INFORMATION FOR SEQ ID NO:39:

( i ) SEQUENCE CHARACTERISTICS:
( A ) LENGTH: 47 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: MTA-4, Fig. 9

( x i ) SEQUENCE DESCRIPTION: SEQ ID NO:39:

```
Cys Gly Phe Pro Ser Ser Leu Leu Val Asp Ala Pro Gly Tyr Asp Pro
1               5                   10                  15

Ile Trp Phe Leu Asn Thr Glu Pro Ser Gln Leu Pro Pro Thr Ala Pro
            20                  25                  30

Pro Leu Leu Pro His Ser Asn Leu Asp His Ile Leu Glu Pro Ser
        35                  40                  45
```

( 2 ) INFORMATION FOR SEQ ID NO:40:

( i ) SEQUENCE CHARACTERISTICS:
( A ) LENGTH: 76 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: MTA-5, Fig. 9

( x i ) SEQUENCE DESCRIPTION: SEQ ID NO:40:

```
Leu Leu Val Asp Ala Pro Gly Tyr Asp Pro Ile Trp Phe Leu Asn Thr
1               5                   10                  15

Glu Pro Ser Gln Leu Pro Pro Thr Ala Pro Pro Leu Leu Pro His Ser
            20                  25                  30

Asn Leu Asp His Ile Leu Glu Pro Ser Ile Pro Trp Lys Ser Lys Leu
        35                  40                  45

Leu Thr Leu Val Gln Leu Thr Leu Gln Ser Thr Tyr Tyr Cys Ile Val
    50                  55                  60

Cys Ile Asp Arg Ala Ser Leu Ser Thr Trp His Val
65                  70                  75
```

( 2 ) INFORMATION FOR SEQ ID NO:41:

( i ) SEQUENCE CHARACTERISTICS:
( A ) LENGTH: 18 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: K163, Fig. 9

( x i ) SEQUENCE DESCRIPTION: SEQ ID NO:41:

-continued

Thr Ala Pro Pro Leu Leu Pro His Ser Asn Leu Asp His Ile Leu Glu
1 5 10 15

Pro Ser ( 2 ) INFORMATION FOR SEQ ID NO:42:

( i ) SEQUENCE CHARACTERISTICS:
( A ) LENGTH: 49 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: K15, Fig. 9

( x i ) SEQUENCE DESCRIPTION: SEQ ID NO:42:

Met Thr Leu Leu Val Asp Ala Pro Gly Tyr Asp Pro Leu Trp Phe Ile
1 5 10 15

Thr Ser Glu Pro Thr Gln Pro Pro Pro Thr Ser Pro Pro Leu Val His
20 25 30

Asp Ser Asp Leu Glu His Val Leu Thr Pro Ser Thr Ser Trp Thr Thr
35 40 45

Lys ( 2 ) INFORMATION FOR SEQ ID NO:43:

( i ) SEQUENCE CHARACTERISTICS:
( A ) LENGTH: 17 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: K34, Fig. 9

( x i ) SEQUENCE DESCRIPTION: SEQ ID NO:43:

Ser Pro Pro Leu Val His Asp Ser Asp Leu Glu His Val Leu Thr Pro
1 5 10 15

Ser ( 2 ) INFORMATION FOR SEQ ID NO:44:

( i ) SEQUENCE CHARACTERISTICS:
( A ) LENGTH: 68 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: MODIFIED pGEX, FIG. 3C ( i x ) FEATURE:
( A ) NAME/KEY: CDS
( B ) LOCATION: 3..68

( x i ) SEQUENCE DESCRIPTION: SEQ ID NO:44:

AT CCT CCA AAA TCG GAT CTG GTT CCG CGT GGT TCC ATG GGT GGA TCC 47
Pro Pro Lys Ser Asp Leu Val Pro Arg Gly Ser Met Gly Gly Ser
1 5 10 15

-continued

GAA TTC ATC GTG ACT GAC TGA 68
Glu Phe Ile Val Thr Asp
20

(2) INFORMATION FOR SEQ ID NO:45:

(i) SEQUENCE CHARACTERISTICS:
(A) LENGTH: 21 amino acids
(B) TYPE: amino acid
(D) TOPOLOGY: linear (ii) MOLECULE TYPE: protein (xi) SEQUENCE DESCRIPTION: SEQ ID NO:45:

Pro Pro Lys Ser Asp Leu Val Pro Arg Gly Ser Met Gly Gly Ser Glu
1 5 10 15

Phe Ile Val Thr Asp
20

(2) INFORMATION FOR SEQ ID NO:46:

(i) SEQUENCE CHARACTERISTICS:
(A) LENGTH: 99 amino acids
(B) TYPE: amino acid
(D) TOPOLOGY: linear (ii) MOLECULE TYPE: protein (iii) HYPOTHETICAL: NO (vi) ORIGINAL SOURCE:
(C) INDIVIDUAL ISOLATE: p21E, Fig. 4

(xi) SEQUENCE DESCRIPTION: SEQ ID NO:46:

Leu Gly Ser Arg Ser Arg Arg Ala Val Pro Val Ala Val Trp Leu Val
1 5 10 15

Ser Ala Leu Ala Met Gly Ala Gly Val Ala Gly Gly Ile Thr Gly Ser
20 25 30

Met Ser Leu Ala Ser Gly Lys Ser Leu Leu His Glu Val Asp Lys Asp
35 40 45

Ile Ser Gln Leu Thr Gln Ala Ile Val Lys Asn His Lys Asn Leu Leu
50 55 60

Lys Ile Ala Gln Tyr Ala Ala Gln Asn Arg Arg Gly Leu Asp Leu Leu
65 70 75 80

Phe Trp Glu Gln Gly Gly Leu Cys Lys Ala Leu Gln Glu Gln Cys Arg
85 90 95

Phe Pro Asn (2) INFORMATION FOR SEQ ID NO:47:

(i) SEQUENCE CHARACTERISTICS:
(A) LENGTH: 63 amino acids
(B) TYPE: amino acid
(D) TOPOLOGY: linear (ii) MOLECULE TYPE: protein (iii) HYPOTHETICAL: NO (vi) ORIGINAL SOURCE:
(C) INDIVIDUAL ISOLATE: 2B3AS, Fig. 5

(xi) SEQUENCE DESCRIPTION: SEQ ID NO:47:

His Glu Val Asp Lys Asp Ile Ser Gln Leu Thr Gln Ala Ile Val Lys
1 5 10 15

-continued

| | | | | | | | | | | | | | | | |
|---|---|---|---|---|---|---|---|---|---|---|---|---|---|---|---|
| Asn | His | Lys | Asn 20 | Leu | Leu | Lys | Ile | Ala 25 | Gln | Tyr | Ala | Ala | Gln 30 | Asn | Arg |
| Arg | Gly | Leu 35 | Asp | Leu | Leu | Phe | Trp 40 | Glu | Gln | Gly | Gly | Leu 45 | Cys | Lys | Ala |
| Leu | Gln 50 | Glu | Gln | Cys | Arg | Phe 55 | Pro | Asn | Ile | Thr | Asn 60 | Ser | His | Val | |

( 2 ) INFORMATION FOR SEQ ID NO:48:

( i ) SEQUENCE CHARACTERISTICS:
( A ) LENGTH: 63 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AM, Fig. 5

( x i ) SEQUENCE DESCRIPTION: SEQ ID NO:48:

| | | | | | | | | | | | | | | | |
|---|---|---|---|---|---|---|---|---|---|---|---|---|---|---|---|
| His 1 | Glu | Val | Asp | Lys 5 | Asp | Ile | Ser | Gln | Leu 10 | Thr | Gln | Ala | Ile | Val 15 | Lys |
| Asn | His | Lys | Asn 20 | Leu | Leu | Lys | Ile | Ala 25 | Gln | Tyr | Ala | Ala | Gln 30 | Asn | Arg |
| Arg | Gly | Leu 35 | Asp | Leu | Leu | Phe | Trp 40 | Glu | Gln | Gly | Gly | Leu 45 | Cys | Lys | Ala |
| Leu | Gln 50 | Glu | Gln | Cys | Cys | Phe 55 | Leu | Asn | Ile | Thr | Asn 60 | Ser | His | Val | |

( 2 ) INFORMATION FOR SEQ ID NO:49:

( i ) SEQUENCE CHARACTERISTICS:
( A ) LENGTH: 63 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 2B3AB, Fig. 5

( x i ) SEQUENCE DESCRIPTION: SEQ ID NO:49:

| | | | | | | | | | | | | | | | |
|---|---|---|---|---|---|---|---|---|---|---|---|---|---|---|---|
| His 1 | Glu | Val | Asp | Lys 5 | Asp | Ile | Ser | Gln | Leu 10 | Thr | Gln | Ala | Ile | Val 15 | Lys |
| Asn | His | Lys | Asn 20 | Leu | Leu | Lys | Val | Ala 25 | Gln | Tyr | Ala | Ala | Gln 30 | Asn | Arg |
| Arg | Gly | Leu 35 | Asp | Leu | Leu | Phe | Trp 40 | Glu | Gln | Gly | Gly | Leu 45 | Cys | Lys | Ala |
| Leu | Gln 50 | Glu | Gln | Cys | Cys | Phe 55 | Leu | Asn | Ile | Thr | Asn 60 | Ser | His | Val | |

( 2 ) INFORMATION FOR SEQ ID NO:50:

( i ) SEQUENCE CHARACTERISTICS:
( A ) LENGTH: 63 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:

( C ) INDIVIDUAL ISOLATE: 2B3AMO, Fig. 5

( x i ) SEQUENCE DESCRIPTION: SEQ ID NO:50:

```
Lys Asp Ile Ser His Leu Thr Gln Ala Ile Val Lys Asn His Gln Asn
1               5                   10                  15

Ile Leu Arg Val Ala Gln Tyr Ala Ala Gln Asn Arg Arg Gly Leu Asp
            20                  25                  30

Leu Leu Phe Trp Glu Gln Gly Gly Leu Cys Lys Ala Ile Gln Glu Gln
        35                  40                  45

Cys Cys Phe Leu Asn Ile Ser Asn Thr His Val Ser Val Leu Gln
    50                  55                  60
```

( 2 ) INFORMATION FOR SEQ ID NO:51:

( i ) SEQUENCE CHARACTERISTICS:
( A ) LENGTH: 53 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BS, Fig. 6

( x i ) SEQUENCE DESCRIPTION: SEQ ID NO:51:

```
Glu Gln Gly Gly Leu Cys Lys Ala Leu Gln Glu Gln Cys Arg Phe Pro
1               5                   10                  15

Asn Ile Thr Asn Ser His Val Pro Ile Leu Gln Glu Arg Pro Pro Leu
            20                  25                  30

Glu Asn Arg Val Leu Thr Gly Trp Gly Leu Asn Trp Asp Leu Gly Leu
        35                  40                  45

Ser Gln Trp Ala Arg
    50
```

( 2 ) INFORMATION FOR SEQ ID NO:52:

( i ) SEQUENCE CHARACTERISTICS:
( A ) LENGTH: 53 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BM, Fig. 6

( x i ) SEQUENCE DESCRIPTION: SEQ ID NO:52:

```
Glu Gln Gly Gly Leu Cys Lys Ala Leu Gln Glu Gln Cys Cys Phe Leu
1               5                   10                  15

Asn Ile Thr Asn Ser His Val Ser Ile Leu Gln Glu Arg Pro Pro Leu
            20                  25                  30

Glu Asn Arg Val Leu Thr Gly Trp Gly Leu Asn Trp Asp Leu Gly Leu
        35                  40                  45

Ser Gln Trp Ala Arg
    50
```

( 2 ) INFORMATION FOR SEQ ID NO:53:

( i ) SEQUENCE CHARACTERISTICS:
( A ) LENGTH: 53 amino acids
( B ) TYPE: amino acid -continued ( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BCH, Fig. 6

( x i ) SEQUENCE DESCRIPTION: SEQ ID NO:53:

```
Glu Gln Gly Gly Leu Cys Lys Ala Leu Gln Glu Gln Cys Cys Phe Leu
1               5                   10                  15

Asn Ile Thr Asn Ser His Val Ser Met Leu Gln Glu Arg Pro Pro Leu
            20                  25                  30

Glu Asn Arg Val Leu Thr Gly Trp Gly Leu Asn Trp Asp Leu Gly Leu
        35                  40                  45

Ser Gln Trp Ala Arg
    50
```

( 2 ) INFORMATION FOR SEQ ID NO:54:

( i ) SEQUENCE CHARACTERISTICS:
( A ) LENGTH: 53 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 3A3BMO, Fig. 6

( x i ) SEQUENCE DESCRIPTION: SEQ ID NO:54:

```
Leu Cys Lys Ala Ile Gln Glu Gln Cys Cys Phe Leu Asn Ile Ser Asn
1               5                   10                  15

Thr His Val Ser Val Leu Gln Glu Arg Pro Pro Leu Glu Lys Arg Val
            20                  25                  30

Ile Thr Gly Trp Gly Leu Asn Trp Asp Leu Gly Leu Ser Gln Trp Ala
        35                  40                  45

Arg Glu Ala Leu Gln
    50
```

METHOD AND ASSAY FOR HTLV

This application is a continuation-in-part of U.S. patent application for "HTLV-I and HTLV-II Peptide Antigens and Methods", Ser. No. 07/653,091, filed Feb. 8, 1991, abandoned, which in turn is a continuation-in-part of U.S. patent application "HTLV-I Peptide Antigen and Methods", Ser. No. 07/366,313, filed Jun. 13, 1989, now U.S. Pat. No. 5,066,579, issued Nov. 19, 1991, which in turn is a continuation of U.S. patent application for "HTLV-I Peptide Antigen and Methods," Ser. No. 06/948,270, filed Dec. 31, 1986, now abandoned.

1. FIELD OF THE INVENTION

The present invention relates to an HTLV-specific peptide and to methods of preparing and using the antigen.

2. REFERENCES

Cann, A. J., and Chen, I. S. Y., Virology (Fields, B. N., ed.), 2nd Edition, Raven Press Ltd., New York, N.Y. pp. 1501 (1990).

Carroll, W. P., et al., J. Immunol. Meth. 89:61 (1986).

Cwirla, S. E., et al., Proc Nat Acad. Sci, USA, 87:6378 (1990).

Foung, S. K. H., et al., J. Immunol. Methods 134:35 (1990).

Hadlock, K. G., et al., Blood 79:190 (1992).

Harlow, E., et al., Antibodies, A Laboratory Manual, Cold Spring Harbor, (1988)

Huse, W., et al., Science, 246:1275 (1989).

Huynh, T. V., et al , in "DNA Cloning, Volume 1," (D. M. Glover, ed.) Washington, D. C.: IRL Press, 1985 (Chapter 2).

Kwok S., et al., Blood. 72:1117 (1988)

Laemmli, U. K., Nature, 227:680 (1970).

Lal, R. B., et al., J. Clin. Microbiol. 30:296 (1992).

Larrick, J. W., et al. (1989) Biotechnology 7:934–938.

Larrick, J. W., et al. Methods in Immunology, 2:106–110 (1992).

Larrick, J. W., et al., Immunol Rev, 130 (1992).

Lillehoj, E. P., et al., J. Clin. Microbiol. 28:2653 (1990).

Lipka, J. J., et al., Proceedings of the 43 Meeting (1990).

Lipka, J. J., et al., J. Infect. Dis. 164:400 (1991).

Lipka, J. J., et al., J. Infect. Dis. 165:268 (1992a).

Lipka, J. J., et al., Proceedings of 5th Ann. Conf. on Human Retrovirology HTLV, Kumamoto, Japan (1992b).

Maniatis, T., et al., *Molecular Cloning: A Laboratory Manual,* Cold Spring Harbor Laboratory (1982).

Matsushita, S., et al., Proc Natl Acad Sci (USA), 83:2672 (1986).

McCafferty, J., et al., Nature 348:552 (1990).

Mitchell A. R., et al., J. Org Chem. 43:245 (1978).

Miyoshi, I., et al., Nature, 294:770 (1981).

Perkins, S., et al., Electromanipulation in Hybridoma Technology, A Laboratory Manual (Borrebazck, I., et al., eds.) Stockton Press, New York, N.Y. pp. 47–70 (1989).

Poiesz, B. J., et al., Proc Natl Acad Sci (USA), 77:7415 (1980).

Popovic, M., et al., Science, 29:856 (1983).

Public health service working group. *MMWR* 37:736. (1988).

Roberts, B. D., et al., Proceedings of 5th Ann. Conf. on Human Retrovirology HTLV, Kumamoto, Japan (1992).

Roberts, B. D., et al., J. Clin. Microbiol., accepted for publication.

Samuel, K. P., et al., Science, 226:1094 (1984).

Samuel, K. P., Gene Anal Tech, 2:60 (1985)

Scott, J. T. et al., Science, 249:386 (1990).

Seiki, M., et al., Proc Natl Acad Sci (USA), 80:3618 (1983).

Shimotokno, K., et al., Proc Nat Acad Sci, USA, 82:3101 (1985).

Urlaub, G. and Chasin, L. A., Proc. Nat. Acad. Sci. (USA) 77:4216 (1980).

3. BACKGROUND OF THE INVENTION

The human T-cell leukemia viruses (HTLV) represent a family of T-cell retroviruses with three known members. HTLV type I (HTLV-I) has transforming activity in vitro and is etiologically linked to adult T-cell leukemia, which is known to be endemic in several parts of the world. HTLV-II is another retrovirus having transforming capacity in vitro, and has been isolated from a patient with a T-cell variant of hairy cell leukemia (for a review of HTLV-I and II see Cann and Chen). HTLV-III, which has also been called lymphadenopathy-associated virus and is now known as the human immunodeficiency virus (HIV), is lytic for certain kinds of T cells and has been linked to the etiology of acquired immunodeficiency syndrome (AIDS). Unlike the HTLV-I and -II viruses, HTLV-III is not known to have in vitro transforming activity.

The diagnosis of HTLV-I infection is usually based on serum antibody response to HTLV-I peptide antigens. This usually involves an initial screening assay to identify HTLV-I antibodies, based on an enzyme immunoassay (EIA) with HTLV-I virion peptides. The assays presently used for blood screening detect about 0.5 to 0.05% HTLV-I and HTLV-II positives in blood donors in the United States; of these about 4 out of 5 are false positives. Therefore, positive sera must be further tested in a confirmatory assay, using Western blotted HTLV-I viral lysate. Current blood testing procedures require that individuals possess antibodies to both the HTLV-I p24 gag protein and at least one of the envelop proteins gp46, and gp68 (public health service working group). However, it has proven to be technically difficult to detect gp46 or gp68 proteins using a Western blot assay. Therefore a second round of confirmatory radioimmunoprecipitation assays must often be performed to detect antibody reaction to the HTLV-I envelope proteins.

A partial solution to this problem was provided by the molecular cloning of a 134 amino acid portion of the transmembrane glycoprotein gp21 (Samuel et al.). The recombinant protein, referred to as p21E protein, is reactive with sera from both HTLV-I and HTLV-II infected individuals, and has been successfully incorporated into Western blot assays for confirmation of HTLV infection (Lillehoj et al., Lipka et al. 1991). However, the p21E protein was also found to be reactive with 0.6% of HTLV negative blood donors (Lal, et al.). In addition, much higher rates of reactivity to p21E (approximately 5% in U.S. blood donors) are observed in individuals who are reactive in HTLV screening EIA tests, but who do not Possess antibodies to both HTLV-I gag and env gene products when tested by HTLV confirmatory assays and thus do not meet established criteria for being HTLV infected (Lal, et al.; Lipka, et al., 1991). Additionally in the study by Lipka et al. (Lipka et al. 1991) all of the p21E reactive-HTLV indeterminate individuals were negative for the presence of HTLV-I and HTLV-II nucleic acids when tested by PCR using HTLV-I and HTLV-II specific primers and probes. Therefore some individuals who are not infected with HTLV-I or HTLV-II possess antibodies which react with the p21E antigen. This fact has limited the use of the p21E recombinant protein, particularly in HTLV screening assays in which a high rate of false positives with HTLV-negative sera would result in the needless disposal of donated blood.

It would therefore be desirable to provide an improved method for detecting HTLV-I and HTLV-II positive sera. In particular, the improved test should be capable of detecting all HTLV-I and HTLV-II positive sera, with a minimum number of false positives, and also be able to distinguish HTLV-I from HTLV-II infected sera.

4. SUMMARY OF THE INVENTION

The invention includes, in one aspect, a peptide having an HTLV-specific antigenic region consisting essentially of the amino acid sequence identified by SEQ ID NO: 1. The peptide is characterized by (i) immunoreactivity to sera from human subjects infected with HTLV-I or HTLV-II, and (ii) non-immunoreactivity with sera that is (1) obtained from humans who are not infected with HTLV-I or HTLV-II, but (2) immunoreactive with HTLV-1 p21E antigen.

Also disclosed is a kit for detecting the presence of HTLV-I or HTLV-II infection in a human serum. The kit includes (a) a solid support, (b) the above HTLV-specific peptide attached to the support, and (c) a reporter reagent for detecting the presence of human antibodies bound to said support.

In one embodiment, for use in detecting HTLV-I or HTLV-II infection, the solid support includes two reaction zones, one coated with the above HTLV-specific peptide, and a second zone coated with a HTLV-specific antigenic region consisting essentially of the amino acid sequence identified by SEQ ID NO: 2. This peptide is characterized by immunoreactivity with sera that is (1) obtained from humans who are not infected with HTLV-I or HTLV-II, but (2) immunoreactive with HTLV-1 p21E antigen.

The kit may also contain one or more reaction zones designed to allow discrimination between HTLV-I and HTLV-II infection. One preferred peptide for use in this kit is a peptide having an HTLV-I specific antigenic region consisting essentially of the sequence identified by SEQ NO ID: 3. Alternatively, or in addition, the kit may include a peptide having an HTLV-II specific antigenic region consisting essentially of the sequence identified by SEQ NO ID: 4.

In another aspect, the invention includes a method of positively identifying HTLV-I or HTLV-II infection in a human subject. The test includes reacting serum from the subject with a peptide containing an HTLV-specific antigenic region consisting essentially of the amino acid sequence identified by SEQ ID NO: 1, to form an immune complex the peptide and antibodies in serum from a subject having an HTLV-I or HTLV-II infection. The peptide is then examined for the presence of the immune complex.

Also disclosed is a vaccine composition for immunizing an individual against HTLV-I and HTLV-II infection. The composition includes a peptide having an HTLV-specific antigenic region consisting essentially of the amino acid sequence identified by SEQ ID NO: 1. The peptide is coupled to an carrier protein.

In still another aspect, the invention includes a passive vaccine from HTLV prophylaxis and treatment, and method of passive vaccination employing a human monoclonal antibody or human recombinant antibody specific against the 2B3A peptide.

These and other objects and features of the present invention will become more fully apparent when the following detailed description of the invention is read in conjunction with the accompanying drawings.

BRIEF DESCRIPTION OF THE DRAWINGS

FIGS. 2A and 2B show the polynucleotide coding sequence (SEQ ID NO: 5) and the corresponding amino acid sequence (SEQ ID NO: 6) for the p21E env protein of HTLV-I (FIG. 2A), and the polynucleotide coding sequence (SEQ ID NO: 7) and the corresponding amino acid sequence SEQ ID NO: 8) for the p21E region of the gp21 env protein of HTLV-II (FIG. 2B). The 5' ends of the HTLV-I specific sequences of the oligonucleotide primers used in the construction of the HTLV-I recombinant peptides are indicated.

FIGS. 3A–3C show the polynucleotide sequences of forward primers (FIG. 3A) identified herein as 1A (SEQ ID NO: 9), 2A (SEQ ID NO: 10), MF1 (SEQ ID NO: 11), MF2 (SEQ ID NO: 12) and 3A (SEQ ID NO: 13), and the reverse primers (FIG. 3B) identified herein as 1B (SEQ ID NO: 14), 2B (SEQ ID NO: 15), MR1 (SEQ ID NO: 16), MR2 (SEQ ID NO: 17), and 3B (SEQ ID NO: 18), where the restriction enzyme recognition sequences located in the primers are underlined. The restriction enzyme sites of the modified pGEX plasmid pGEX-GLI are also presented (SEQ ID NO: 44) (FIG. 3C).

FIG. 4 shows the amino acid sequences of the HTLV-I recombinant peptides identified as p21E (SEQ ID NO: 46), 1A1B (SEQ ID NO: 19), 2A2B (SEQ ID NO: 20), 2A3B (SEQ ID NO:21), 2B3A (SEQ ID NO: 22), 3A3B (SEQ ID NO: 30), MF1R2 (SEQ ID NO: 24), and MF2R1 (SEQ ID NO: 25).

FIG. 5 shows the amino acid sequences of the peptide 2B3A which was actually constructed (SEQ ID NO: 22) and the corresponding sequence from three different HTLV-I strains (SEQ ID NOS: 26, 27, and 28), a corresponding HTLV-II 2B3A peptide (SEQ ID NO: 29), and the consensus sequence for the 2B3A peptide (SEQ ID NO: 1).

FIG. 6 shows the amino acid sequences of the peptide 3A3B which was actually constructed (SEQ ID NO: 23) and the corresponding sequence from three different HTLV-I strains (SEQ ID NOS: 31, 32, and 2), a corresponding HTLV-II 3A3B peptide (SEQ ID NO: 34), and the consensus sequence for the 3A3B peptide (SEQ ID NO: 2).

FIG. 7 shows a comparison of the polynucleotide coding sequences for the HTLV-I peptide 2B3A (SEQ ID NO: 35) and the homologous HTLV-II peptide 2B3A(II) (SEQ ID NO: 36).

FIG. 8 shows a comparison of the polynucleotide coding sequences for the HTLV-I peptide 3A3B (SEQ ID NO: 37) and the homologous HTLV-II peptide 3A3B(II) (SEQ ID NO: 38).

FIG. 9 shows the amino acid sequences of homologous regions of HTLV-I and HTLV-II gp46 protein in the region of the gp46 peptides identified in FIG. 1 as MTA-1 (SEQ ID NO: 3), MTA-4 (SEQ ID NO: 39), and MTA-5 (SEQ ID NO: 40), additional HTLV-I peptide K163 (SEQ ID NO: 41), and analogous HTLV-II peptides identified herein as K15 (SEQ ID NO: 42) and 4 (SEQ ID NO: 4).

DETAILED DESCRIPTION OF THE INVENTION

I. Definitions

Unless indicated otherwise, the terms given below have the following meanings:

"HTLV-composite env sequence" is formed by aligning homologous amino acid sequences of regions of the env transmembrane protein of different strains of HTLV-I and HTLV-II, and selecting, at each position (i) the consensus amino acid at that position, or (ii) if the amino acids at that position are different among the HTLV-I and HTLV-II sequences, all of the amino acid variations at that position. For example, the 2B3A HTLV composite sequence shown in FIG. 5 contains amino acid variations within the amino acid sequences of the 2B3A peptide for three different HTLV-I strains (SEQ ID NOS: 26, 27, and 28), a corresponding HTLV-II 2B3A peptide (SEQ ID NO: 29), and the consensus sequence for the 2B3A peptide (SEQ ID NO: 1).

"HTLV-specific" peptide means a peptide having an HTLV composite sequence, i.e., either an HTLV-I amino acid sequence, and HTLV-II amino acid sequence, or one of the HTLV composite sequences.

"Non-infected individuals" refers to humans whose serum may contain antibodies which are crossreactive with some HTLV-I or HTLV-II proteins, e.g., p21E protein, but whose serum shows no evidence of HTLV-I or HTLV-II infection, as judged by 1.> Failure to detect antibodies to both HTLV gag and env proteins in a confirmatory assay and/or 2.> the failure to detect HTLV-specific sequences by sequence amplification with HTLV-specific primers using the polymerase chain reaction (PCR) method (Kwok et al., Lipka et al. 1991).

II. HTLV-I and HTLV-II Env Peptides

Figure 1:
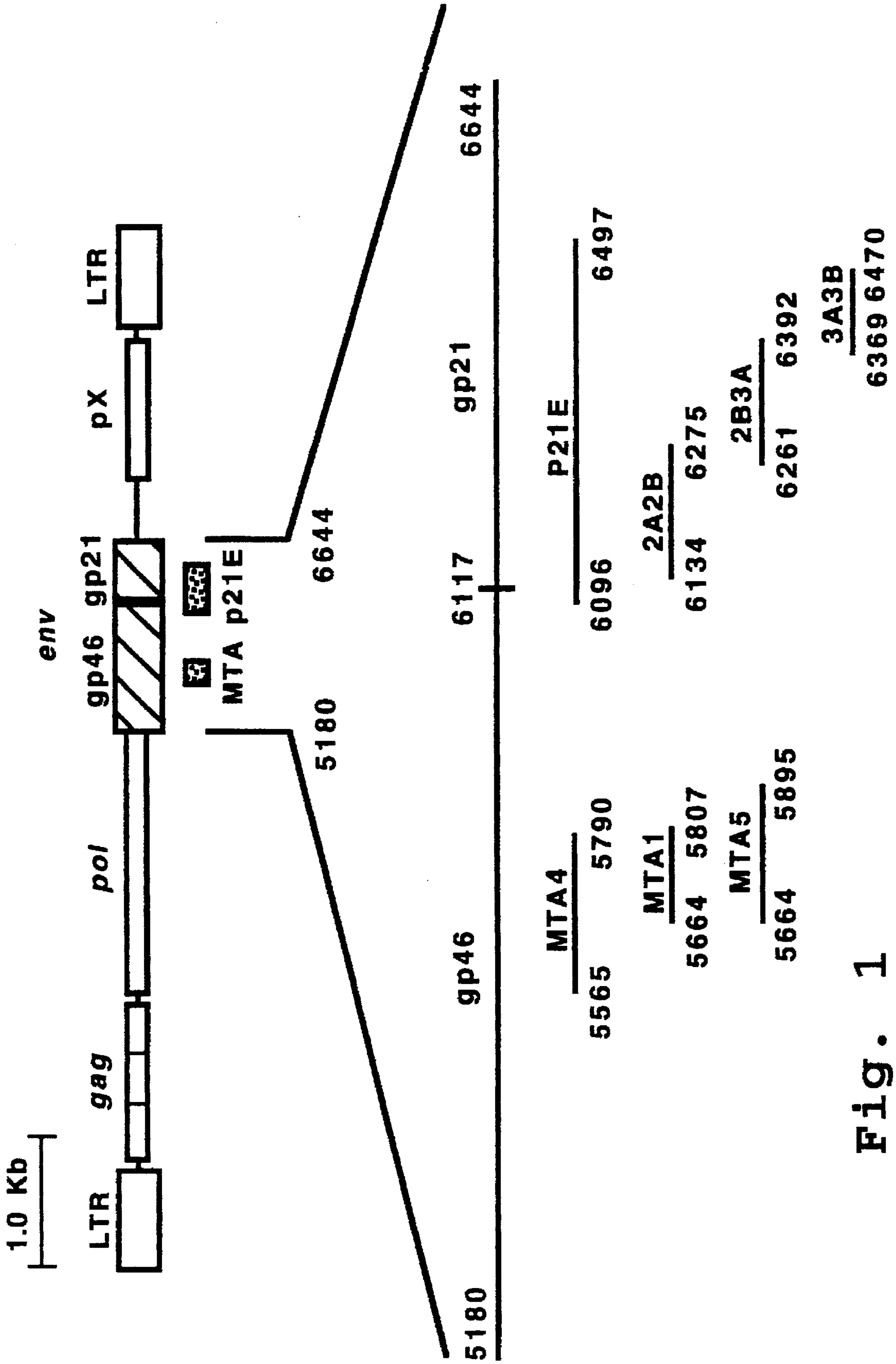
FIG. 1 shows, at the top, the HTLV-I genome, in the middle, an expanded portion of the genome containing the coding regions for gp46 and gp21 envelope proteins, and in the lower portion of the figure, the coding regions corresponding to recombinant HTLV-I peptides p21E, 2A2B, 2B3A, and 3A3B within the gp21 coding region, and the HTLV-I MTA-1, MTA-4, and MTA-5 peptides in the gp46 coding region.

FIG. 1, upper frame, represents a portion of an HTLV-I genome which is expressed in the env transmembrane glycoproteins gp46 and gp21. The coding region extends from basepair 5180 to 6116 for gp46, and between 6117 and 6644 for the gp21 protein (expanded portion of the genome in FIG. 1).

The coding region between bases 6096 and 6497 encodes a recombinant protein, designated p21E, which is known to react with sera from HTLV-I or HTLV-II infected individuals, but which is also reactive with a small percentage of individuals who are not infected with either HTLV virus (Lal et al., Lipka et al., 1991). Contained within the p21E coding region, and shown at the lower right in the figure, are coding regions for three HTLV-I peptides identified herein as 2A2B, 2B3A, and 3A3B. The present invention includes the 2B3A peptide, and a diagnostic assay kit and method which includes the 2B3A peptide. The kit and method may also include the 3A3B peptide. The properties of the 2B3A and 3A3B peptides which are related to the assay kit and method for detecting to the HTLV-I or HTLV-II infected human sera are discussed below.

The coding region 5565 to 5895, shown at the lower left in the figure contains coding regions for three MTA peptides described in co-pending U.S. patent application for "HTLV-I and HTLV-II Peptide Antigens and Methods", Ser. No. 07/653,091, filed Feb. 8, 1991, and identified in the co-pending application and herein as MTA-1, MTA-4, and MTA-5. These peptides may also be used, in combination with the 2B3A peptide, or the 2B3A peptide plus the 3A3B peptide, in an assay kit and method for assaying for HTLV-I or HTLV-II infected human sera. The properties of the MTA peptides which are pertinent to the use in such a kit and method are given below.

A. 2B3A Peptide

FIG. 4 shows the amino acid sequences of a 2B3A peptide from HTLV-I (SEQ ID NO: 22). As will be seen below, the peptide was expressed by PCR amplification of an HTLV-I, strain MT2 virus, using primers (which contribute 7 codons on each end of the amplified coding region) designed from the nucleotide coding sequence of the HTLV-I variant ATK isolated by Seiki et al. Thus, the seven amino acids at either end of the peptide correspond in sequence to the 2B3A peptide from the HTLV-I strain ATK and the remaining interior amino acids correspond in sequence to the 2B3A peptide from HTLV-I, strain MT2. The single-letter and triple-letter amino acid codes in the figure conform to standard convention (e.g., Maniatis).

According to an important aspect of the invention, and as detailed below, the peptide is (i) immunoreactive with sera from human subjects infected with HTLV-I or HTLV-II, but (ii) not immunoreactive with sera that is immunoreactive with HTLV-1 p21E antigen, but which shows no evidence of HTLV-I or HTLV-II infection, for example, by PCR analysis of viral sequences in the serum sample, as discussed below.

FIG. 5 shows the amino acid sequences of peptides containing the 2B3A for three different HTLV-I strains, identified herein as ATK, MT2, and B41281, and one HTLV-II peptide, identified herein as strain MO. These nucleotide and amino acid sequences of these HTLV variants were obtained from the Genbank sequence data base. The locus names of the strains which can be used to obtain the sequences from the Genbank data base are as follows; HTLV1A=env region of the HTLV-I variant ATK, HTVENVAA=env region of the HTLV-I variant MT2, B41281=another more divergent HTLV-I isolate, and HL3V2CG=MoT strain of HTLV-II. The figure also shows the amino acid sequence matching between the upper 2B3A sequence and the corresponding regions of the three HTLV-I strains and the one HTLV-II strain. The sequence homology between the uppermost 2B3A peptide and the corresponding portion of the individual-strain gp21 protein is shown directly above the amino acid sequence of each strain. The degree of homology is indicated by ":" for identical sequences and a blank for non-matching amino acids residues.

The 2B3A sequences (i.e., the portions of the gp21 amino acid sequences corresponding to the HTLV-I peptide antigen 2B3A) are identified in the figure as follows; SEQ ID NO: 26=ATK variant of HTLV-I; SEQ ID NO: 28=MT2 variant of HTLV-I, and SEQ ID NO: 28=the HTLV variant identified by the locus name B41281. The corresponding HTLV-II 2B3A peptide from strain Mo is identified herein by SEQ ID NO: 29. The strains displayed in FIG. 5 and FIG. 6 below are representative of the different amino acid sequences obtained from approximately 30 separate variants of HTLV-I, STLV, and HTLV-II (the amino acid and nucleotide sequences of all of the variants can be obtained from the Genbank database).

The consensus sequence of the five 2B3A sequences, i.e., the HTLV composite sequence for this region, is shown at the bottom of the figure, and is identified herein by SEQ ID NO: 1. This sequence is constructed from the consensus amino acids, where there is complete consensus among the five peptides, and by the known variations in amino acid, at the six positions ($X_1$–$X_6$) where amino acid variations occur. In this sequence $X_1$ is K or Q, $X_2$ is L or I, $X_3$ is K or R, $X_4$ is I or V, and $X_5$ is R or C, and $X_6$ is P or L. SEQ ID NO: 1 thus includes the five sequences identified above as SEQ ID NO: 22, SEQ ID NOS: 26, SEQ ID NO: 28, SEQ ID NO: 28, and SEQ ID NO: 29. It is to be expected that amino acid substitutions other than those specifically included in SEQ ID NO: 1 may also be allowed, so long as they do not substantially affect the immunoreactivity of the 2B3A peptide as described below. More generally, the 2B3A peptide of the invention includes an HTLV-specific peptide consisting essentially of the amino acid sequence identified by SEQ ID NO: 1, where the peptide is characterized by:

(i) immunoreactivity to sera from human subjects infected with HTLV-I or HTLV-II, and (ii) non-immunoreactivity with sera that is (1) immunoreactive with HTLV-1 p21E antigen, but (2) obtained from humans who are not infected with HTLV-I or HTLV-II.

B. 3A3B Peptide

The 3A3B peptide from HTLV-I has the upper amino acid sequence shown in FIG. 4, and is identified by SEQ ID NO: 30. The peptide is intended, in combination with the 2B3A peptide, for use in an assay kit and method for screening human sera for HTLV-I or HTLV-II infection.

As noted above, sera obtained from patients infected with HTLV-I or HTLV-II contain antibodies which are immunoreactive with the HTLV-I gp21 protein and the p21E recombinant protein derived from gp21. Accordingly, these peptides have been employed routinely in immunoassay methods and kits for detecting HTLV (I or II) infection in humans. The peptides, however, also are crossreactive with antibodies contained in the serum of a certain percentage non-infected individuals, giving false positives in the assay. The frequency of crossreactivity appears to be about 1% of HTLV-negative blood donors, at least in particular locals in the U.S. where statistics are available.

The 2B3A peptide described above is immunoreactive with sera from HTLV-infected individuals, but is not immunoreactive with non-infected individuals, as discussed above. This peptide this provides a useful antigen for detecting HTLV infection without the false positives generated by the p21E protein. It would be further useful, in an HTLV assay, to provide a protein which detects non-infected p21E positive individuals, but not HTLV-infected individuals, as a confirmation that the serum tested is non-infected, even though it is crossreactive with the p21E protein.

The 3A3B peptide described herein has the desired properties, in that the peptide is characterized by immunoreactivity with sera that is (1) obtained from humans who are not infected with HTLV-I or HTLV-II, but (2) immunoreactive with HTLV-1 p21E antigen.

This peptide was expressed by a coding region sequence by PCR amplification of an HTLV-I, strain MT2 virus, using primers (which contribute 7 codons on each end of the amplified coding region) from the HTLV-I variant ATK. Thus, the seven amino acids at either end of the peptide correspond in sequence to the 3A3B peptide from the HTLV-I variant ATK, and the remaining interior amino acids correspond in sequence to the 3A3B peptide from HTLV-I, strain MT2. The corresponding peptide from HTLV-II, designated herein as SEQ ID NO: 34 has amino acid sequence shown at the top in FIG. 6, and is identified herein as SEQ ID NO: 34.

FIG. 6 shows the amino acid sequences of peptides containing the 3A3B for three different HTLV-I strains. The 3A3B sequences are identified in the figure as follows; SEQ ID NOS: 31=ATK variant of HTLV-I; SEQ ID NO: 32=MT2 variant of HTLV-I, and SEQ ID NO: 33=the HTLV variant identified by the locus name HTVENVCH. The corresponding HTLV-II 3A3B peptide from strain Mo is identified herein by SEQ ID NO: 34. These nucleotide and amino acid sequences of the strains were obtained from the Genbank database as described above.

The figure also shows the amino acid sequence matching between the upper 3A3B sequence and the corresponding regions of the three HTLV-I strains and the one HTLV-II strain. The sequence homology between the uppermost 3A3B peptide and the corresponding portion of the individual-strain gp21 protein is shown directly above the amino acid sequence of each strain. The degree of homology is indicated by ":" for identical sequences and a blank for non-matching amino acids residues.

The consensus sequence of the five 3A3B sequences, i.e., the HTLV composite sequence for this region, is shown at the bottom of the figure, and is identified herein by SEQ ID NO: 2. As above, this sequence is constructed from the consensus amino acids, where there is complete consensus among the five peptides, and by the known variations in amino acid, at the eight positions ($X_1$–$X_8$) where amino acid variations occur. In this sequence $X_1$ is R or C, $X_2$ is P or L, $X_3$ is T or S, $X_4$ is S or T, $X_5$ is S or P, $X_6$ is I, M, or V, $X_7$ is N or K, and $X_8$ is L or I. SEQ ID NO: 2 thus includes the five sequences identified above as SEQ ID NO: 30, SEQ ID NOS: 31, SEQ ID NO: 32, SEQ ID NO: 33, and SEQ ID NO: 34. It is anticipated that amino acid substitutions other than those included in SEQ ID NO: 2 may also be allowed, so long as they do not substantially affect the immunoreactivity of the 3A3B peptide as described below. More generally, the 3A3B peptide includes an HTLV-specific peptide consisting essentially of the amino acid sequence identified by SEQ ID NO: 2, where the peptide is characterized by immunoreactivity with sera that is (1) immunoreactive with HTLV-1 p21E antigen, but (2) obtained from humans who are not infected with HTLV-I or HTLV-II.

C. HTLV-I and HTLV-II Specific Peptides

The 2B3A peptide, and the combination of the 2B3A and 3A3B peptides described above are designed for use in an immunoassay method and kit for detecting HTLV-I or HTLV-II infected human sera. The HTLV-I MTA peptides and corresponding gp46 peptides from HTLV-II described in this section are useful in such an assay and kit for distinguishing between infection by HTLV-I and infection by HTLV-II infection.

The preparation and properties of the MTA peptides and the corresponding HTLV-II peptides have been described in co-pending U.S. patent application for "HTLV-I and HTLV-II Peptide Antigens and Methods", Ser. No. 07/653,091, filed Feb. 8, 1991, and corresponding PCT patent application pct/us92/00823, published Aug. 20, 1992, both of which are incorporated herein by reference. The coding regions of MTA peptides identified as MTA-1, MTA-4, and MTA-5 are given in FIG. 1, and encompass the region between bases 5565 and 5895.

FIG. 9 shows the amino acid sequences of MTA-1 (SEQ ID NO: 3), MTA-4 (SEQ ID NO: 39), and MTA-5 (SEQ ID NO: 40). All three peptides are immunoreactive specifically with HTLV-I infected sera, i.e., are not immunoreactive with HTLV-II infected sera. One smaller HTLV-I peptide, identified in FIG. 10 as K163 (SEQ ID NO: 41) is also immunoreactive specifically with HTLV-I infected sera.

The lower portion of FIG. 9 shows corresponding HTLV-II sequences which are specifically immunoreactive with HTLV-II sera, i.e., don't show immunoreactivity with sera from patients infected with HTLV-I only. These include K15 (SEQ ID NO: 42), K34 (SEQ ID NO: 43), and 4 (SEQ ID NO: 4). The smaller peptide antigen, K34 has been shown to have essentially the same immunoreactivity to HTLV-II infected sera as do the larger peptide antigens K15 and K55.

The HTLV-I and HTLV-II specific peptides described in above may be prepared by the recombinant methods described in the above-cited PCT application PCT/US92/00823.

II. Identification of 2B3A and 3A3B Peptides

The p21E polynucleotide coding sequence, identified herein as SEQ ID NO: 5, is shown in FIG. 2, and extending from base 6096 to 6497 was derived from a p21E cloning vector (Samuel et al.). A number of peptides within this region were tested for their immunoreactivity with HTLV-I and HTLV-II infected sera, and with non-infected sera which is immunoreactive with p21E peptide.

A. Preparation of Bacterial Lysates

The peptides which were constructed are shown in FIG. 4. These include recombinant peptides identified as p21E (SEQ ID NO: 6), 1A1B (SEQ ID NO: 19), 2A2B (SEQ ID NO: 20), 2A3B (SEQ ID NO: 21), 2B3A (SEQ ID NO: 22), 3A3B (SEQ ID NO: 30), MF1R2 (SEQ ID NO: 24), AND MF2R1 (SEQ ID NO: 25).

The peptides were prepared by (i) PCR amplification of the selected coding region from the HTLV-I strain MT2, insertion of the amplified coding sequence in a pGEX-GLI expression vector, and transformation of competent *E. coli* host cells with the expression vector, as detailed in Example 1A.

FIGS. 3A and 3B show the sequences of the four forward and four reverse primers, respectively, used in construction the peptide coding regions. These include forward primers identified as FP-1A (SEQ ID NO: 9), FP-2A (SEQ ID NO: 10), FP-MF1 (SEQ ID NO: 11), and FP-3A (SEQ ID NO: 13), and the reverse primers identified herein as RP-1B (SEQ ID NO: 14), RP-2B (SEQ ID NO: 15), RP-MR1 (SEQ ID NO: 16), and RP-3B (SEQ ID NO: 18). The 5' ends of the primers are equipped with recognition sequences for one or more of the following restriction enzymes Nco I, BamH I, and EcoR I. The amplified DNAs can then be cut with the appropriate restriction enzymes for ligation into a similarly digested pGEX-GLI expression vector. The cloning site of pGEX-GLI is also presented in FIG. 3C.

Each selected peptide coding region is constructed by PCR amplification with a selected forward and reverse primer. For example, to construct the coding region of the 1A1B peptide, forward primer FP-1A and reverse primer RP-1B are used to amplify the p21 coding sequence. To construct the coding region of the 2B3A peptide, forward primer MF1 and reverse primer MR1 are employed in PCR amplification of the sequence.

B. Screening of Bacterial Lysates

The recombinant peptides from above were screened in a Western blot assay format described in Example 1C. Briefly, whole cell bacterial lysate transformed with a selected expression vector was fractionated by SDS/PAGE (Laemmli), electroblotted onto nitrocellulose and examined for immunoreactivity with (i) anti-HTLV-I antibodies obtained from EBV-activated lymphocytes from HTLV-I infected individuals (Example 1B), and (ii) HTLV-infected and control sera. Details are given in Example 1C below.

The results are shown in Table 1 below. In the table "ND" means "not done"; "I" indicates sera from an HTLV-I infected individual; "II" indicates sera from an HTLV-I infected individual, where the diagnosis of HTLV-I and HTLV-II was confirmed by PCR; "UnInf" indicates sera from an uninfected individual. "Sup" indicates tissue culture supernatant (diluted 1:2) from a culture of EBV activated peripheral B-cells from an HTLV-I positive donor; and "Ind" indicates sera that are reactive with the recombinant protein p21E, but that are negative for the presence of HTLV-I or HTLV-II infection by PCR using HTLV-I and HTLV-II specific primers and probes.

TABLE 1

| Sera | Type | p21E | 1A1B | 2A3B | 2A2B | 2B3A | 3A3B |
|---|---|---|---|---|---|---|---|
| J254 | I | + | + | + | − | + | − |
| J253 | I | + | − | + | − | + | − |
| J183 | I | + | ND | + | − | + | − |
| J313 | I | + | − | + | − | + | − |
| J103 | I | + | − | + | − | + | + |
| J332 | II | + | − | + | − | + | − |
| J317 | II | + | − | + | − | + | + |
| J309 | II | + | − | + | − | + | − |
| GE9 | Sup | + | − | + | − | + | − |
| 5E4 | Sup | + | − | + | − | + | − |
| J376 | Uninf | − | − | − | − | − | − |
| JCO1 | Ind | + | ND | + | − | − | + |
| JCO2 | Ind | + | ND | + | − | − | + |
| JCO3 | Ind | + | ND | + | − | − | + |
| JCO4 | Ind | + | ND | + | − | − | + |
| JCO5 | Ind | + | ND | + | − | − | + |
| JCO6 | Ind | + | ND | + | − | − | + |
| JCO7 | Ind | + | ND | + | − | − | + |

Overall sera from 10 of the 10 HTLV-I/II infected individuals tested reacted strongly with the relatively large p21E recombinant protein 2A3B. However, only 2 out of the 10 HTLV-I/II antisera tested reacted with either the 2A2B or the 3A3B recombinant proteins. Similarly, when the anti-p21E EBV activated B cell line tissue culture supernatants were tested they both reacted with the recombinant protein 2A3B but not either 2A2B or 3A3B. This suggests that the central portion of 2A3B contains the immunodominant epitope of HTLV-I gp21.

This was confirmed when the recombinant protein 2B3A, which contained 44 amino acids from the central portion of the 2A3B was tested. Ten of the 10 HTLV-I/II sera tested reacted with the 2B3A recombinant protein. In addition, both of the anti-p21E EBV activated B cells tested produced antibodies which recognized the 2B3A.

The location of the epitope recognized by sera that react with the p21E recombinant protein, but are negative for HTLV-I or HTLV-II nucleic acids by PCR was also determined. Seven of 7 p21E indeterminate sera reacted with the 2A3B and 3A3B recombinant proteins. None of the 7 p21E indeterminate sera reacted with the 2B3A recombinant protein. Thus the epitopes recognized by sera from HTLV-I infected individuals and individuals who are not infected, but possess an antibody recognizing p21E are differentiatable.

With reference again to FIG. 4, it is seen that the 2B3A peptide is divided roughly in half by the MF1R1 and MF2R2 peptides. Preliminary studies conducted in support of the invention indicated that neither peptide is immunoreactive with 2 HTLV-I and 2 HTLV-II sera that reacted strongly with the 2B3A peptide. This indicates that the majority of the sequences of the 2B3A peptide are required for immunoreactivity with HTLV positive sera.

C. Preparation of Purified Proteins

Recombinant 2A2B, 2B3A, and 3A3B peptides were prepared from bacterial lysates of transformed bacteria, as detailed in Example 1D. Briefly, the cells were grown under conditions which induced the expression of recombinant protein, pelleted by centrifugation, and lysed by several cycles of freezing and thawing. After lysis, proteins were solubilized by addition of Triton-X100™ and insoluble cellular debris was pelleted by centrifugation.

The supernatant fraction was passed over a glutathione agarose column, and bound proteins were eluted with 5 mM glutathione. Protein containing fractions were pooled. The pooled protein fractions were largely homogeneous, as determined by SDS/PAGE analysis of the protein fractions.

It will be appreciated that the 2B3A and 3A3B peptides may be prepared directly, by solid-phase peptide synthesis methods, e.g., as described by Mitchell et al., or by alternative recombinant systems.

D. Immunoreactivity of Purified Proteins

The purified 2A2B, 2B3A, and 3A3B peptides from above were examined in a Western blot format for immunoreactivity with 56 sera from HTLV-positive individuals, 7 sera from HTLV negative individuals, and 18 sera from p21E reactive, HTLV indeterminate individuals, as identified in Table 2 below. As seen, the 2B3A peptide was immunoreactive with all of the HTLV-I and HTLV-II positive sera, but was not crossreactive with non-infected sera. By contrast, the 3A3B peptide was reactive with some of the HTLV-positive sera, but reacted with all 18 of the non-infected sera (which were also immunoreactive with the p21E peptide).

TABLE 2

| | p21E Recombinant Proteins | | |
|---|---|---|---|
| Sera | 2A2B | 2B3A | 3A3B |
| HTLV-I Infected PCR + | 1/8 | 26/26 | 14/26 |
| HTLV-II Infected PCR + | 0/8 | 28/28 | 19/28 |
| p21E Immunoreactive HTLV PCR (−) | 4/16 | 0/18 | 18/18 |
| HTLV Negative/p21E Negative | 0/1 | 0/7 | 1/7 |

IV. HTLV-I and HTLV-II Diagnostic Method and Kit

Four basic types of diagnostic applications of the 2B3A peptide (defined to include the composite 2B3A peptide) of the invention will be described.

The First general assay type is an enzyme-immunoassay for screening human sera for HTLV-I or HTLV-II infection. In this assay format, a solid phase reagent having surface-bound 2B3A peptide is reacted with analyte serum, under conditions which allow antibody binding to the peptide on the reagent. The assay may also utilize additional HTLV peptides, either recombinant or derived from HTLV viral lysate, bound to the solid phase. After washing the reagent to remove unbound serum components, the reagent is reacted with an reporter-labeled anti-human antibody, to bind reporter to the reagent in proportion to the amount of anti-HTLV-I or HTLV-II specific antibody bound to the 2B3A peptide and any other HTLV peptide(s) also bound to the solid support. The reagent is again washed, to remove unbound antibody, and the amount of reporter associated with the reagent is determined. The reporter-labeled antibody, and additional reagents which may be required for reporter detection, are also referred to herein as reporter means for detecting the presence of human antibody bound to the peptide antigen on the solid support.

The second assay type is an enzyme immunoassay for both detecting antibodies to HTLV-I and HTLV-II and differentiating HTLV-I and HTLV-II infected individuals. In this assay format, recombinant peptide antigens capable of specifically detecting antibodies against HTLV-I, or HTLV-II, or both HTLV-I and HTLV-II are attached to a solid phase reagent at different locations. Duplicate samples of the serum to be tested are added to the appropriate regions of the solid phase reagent, after which the assay is preformed essentially as described above.

Figure 10A:
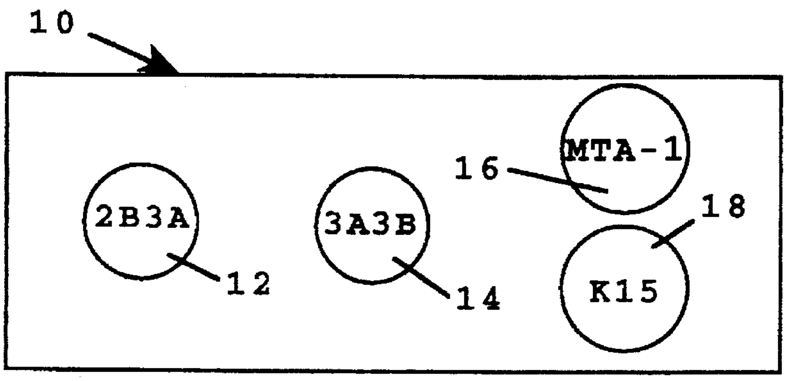
FIGS. 10A–10D illustrate a 4-zone solid phase assay plate for use in an assay method for detecting HTLV-I or HTLV-II infection in human sera (10A), showing a typical assay result for an HTLV-I positive individual (FIG. 10B), for an HTLV-II positive individual (FIG. 10C), and for a false positive (FIG. 10D).

FIG. 10A illustrates a specific embodiment of a solid phase reagent of the this type. The reagent includes a solid support 10 which forms part of a kit for use in detecting HTLV-I or HTLV-II infection in human serum samples. The support has first, second, third, and fourth reaction zones, indicated at 12, 14, 16, and 18, respectively. Reaction zone 12 has surface attached 2B3A peptide molecules. This zone is immunoreactive with antibodies from HTLV-positive serum samples (HTLV-I or HTLV-II infection), but not with "false positives" which are immunoreactive with the p21E peptide but show no evidence of HTLV-I or HTLV-II infection.

Reaction zone 14 has surface attached 3A3B peptide molecules. This zone is immunoreactive with antibodies which are crossreactive with the HTLV-I p21E peptide, but in which the serum itself shows no evidence of HTLV-I or HTLV-II infection, e.g., by PCR detection of HTLV-specific sequences.

Reaction zone 16 has surface attached peptide molecules which are immunoreactive specifically with serum antibodies from HTLV-I infected individuals. One preferred HTLV-I peptide is the MTA-1 peptide identified above (SEQ ID NO: 3). A variety of related gp46 peptides, including MTA-4, MTA-5, and K163 (all shown in FIG. 11) may also be employed.

Reaction zone 18 has surface attached peptide molecules which are immunoreactive specifically with serum antibodies from HTLV-II infected individuals. One preferred HTLV-I peptide is the K55 peptide identified above (SEQ ID NO: 4). Other preferred HTLV-II peptides are the K15 and K34 peptides identified above (SEQ ID NO: 4 and SEQ ID NO: 43).

The solid surface reagent in the above assay is prepared by known techniques for attaching protein material to solid support material, such as a polymer support or the like. The support may be provided with reactive surface groups, such as amine aldehyde, carboxyl, alcohol, or sulfhydryl groups. The peptide attachment methods generally include non-specific adsorption of the protein to the support, or covalent attachment of the protein, typically through a free amine group, to a chemically reactive group on the solid support, such as an activated carboxyl, hydroxyl, or aldehyde group. Methods for attaching peptides to solid support surface, either by non-specific adsorption, or chemical derivatization, are well known.

In a typical assay method, a suitable dilution of a serum sample is placed in contact with each of the four reaction zones in the solid-phase reagent. Generally, the serum sample is placed on each zone in an amount sufficient to cover the zone, e.g., 50–200 μl serum sample. The serum is incubated with the reagent under conditions sufficient to allow immunoreaction of the serum antibodies with the support-bound peptides. Typically reaction conditions are at 37° C. for 30–60 minutes.

Following incubation, the reagent is washed with physiological buffer of the like to remove non-bound and non-specifically bound serum material. To each of the washed zones is then added a drop of detection reagent(s), such as enzyme-labeled anti-human antibody, to bind enzyme to the reagent in proportion to the amount of bound anti-HTLV-I antibody on the solid support. The reagent is again washed, to remove unbound antibody, and the amount of enzyme associated with the reagent is determined.

Figure 10B:
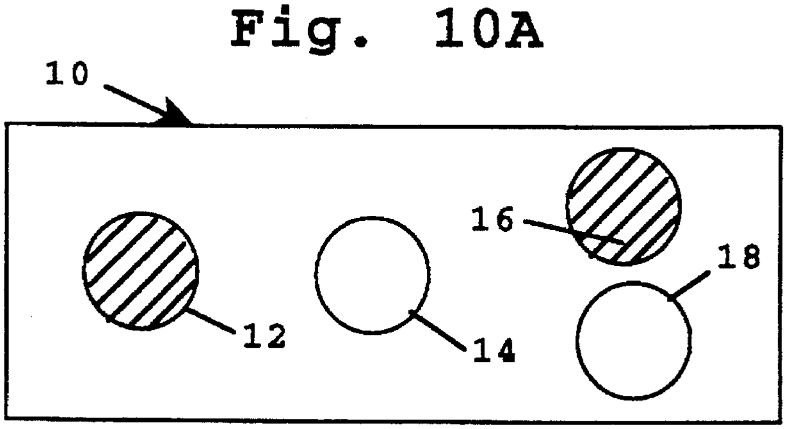

FIG. 10B illustrates the reaction-zone pattern which may be observed in a serum sample from an HTLV-I infected individual, where the cross-hatching indicates a detectable immunoreaction. In the present case, no reaction with the second zone has occurred, although some HTLV-I samples may be immunoreactive with the 3A3B peptide in the second zone (Table 2 above). The reaction with the third, but not the fourth zone, indicates infection by HTLV-I only.

Figure 10C:
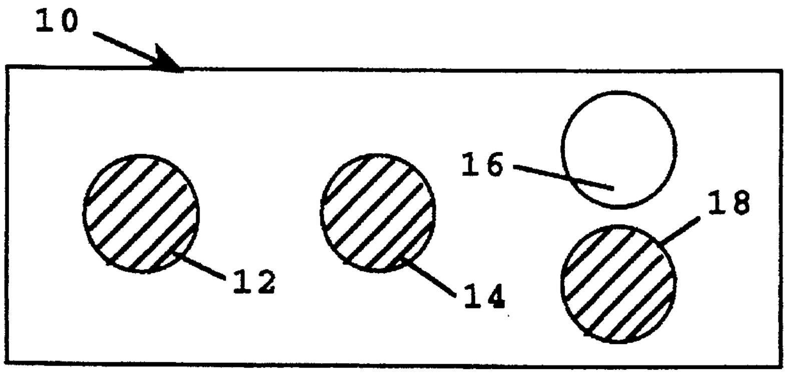

FIG. 10C illustrates the reaction-zone pattern which may be observed in a serum sample from an HTLV-II infected individual. In this case, the serum antibodies are immunoreactive with the 3A3B peptide as well as the 2B3A peptide (Table 2 above). The reaction with the fourth, but not the third zone, indicates infection by HTLV-II only.

Figure 10D:
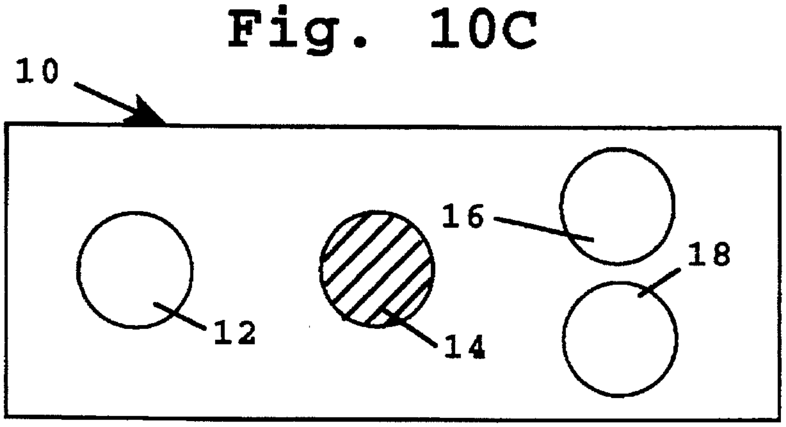

Finally, FIG. 10D illustrates the reaction-zone pattern which may be observed in a serum sample from a non-infected, but cross-reactive serum. The absence of reaction with the first zone indicates no infection by HTLV-I or HTLV-II, even though the serum contains a cross-reactive antibody which recognizes the 3A3B peptide. The absence of reaction with either the third or fourth zones further confirms the absence of HTLV-I or HTLV-II infection in the test serum.

A third general assay type is a Western blot assay for use in confirming HTLV-I or HTLV-II antisera. This assay format includes, in addition to one of the g21 peptide antigens described in this invention, one or more gp46 recombinant peptides, described in U.S. Pat. No. 5,066,579 and PCT patent application PCT/US92/00823 that are effective at detecting and differentiating serum antibodies to HTLV-I and HTLV-II. In one preferred format, the confirmatory peptides include the p24 gag protein from HTLV-I viral lysate and the p21E recombinant envelope protein containing a large portion of the HTLV-I gp21 envelope protein. The HTLV-I viral lysate detects almost all sera containing antibodies to HTLV-I and/or HTLV-II gag proteins. Antibodies to the HTLV-I and HTLV-II env region are detected by the p21E recombinant protein, however, some sera from uninfected individuals will also react with the p21E protein (Lal, et al.; Lipka, et al., 1991). The sera is diagnosed as being infected with HTLV-I or HTLV-II by the reactivity it displays towards the HTLV-I gp46 peptide antigen MTA1 and the HTLV-II gp46 peptide antigen K55. Thus, if a particular infected serum reacts with MTA1 and not K55 the individual is infected with HTLV-I. If the reverse is true the individual can be diagnosed as being infected with HTLV-II. Evaluations of this Western blot confirmatory assay have been reported by the applicants and co-works (Roberts, et al.; Lipka, et al., 1992b). In these studies the described assay had a specificity of 99% and a sensitivity of 99% for detecting HTLV-I and HTLV-II infected individuals. Details of the blot procedure are given in Example 2B and in the cited publications.

In another embodiment of the Western blot assay the p21E recombinant protein is replaced by the gp21 peptide 2B3A described in this invention. In this format either the HTLV-I or HTLV-II version of the 2B3A peptide detects antibodies to either the HTLV-I or HTLV-II gp21 protein. Due to the lack of reactivity of the 2B3A peptide with sera from uninfected individuals who crossreact with the p21E recombinant protein, this assay would be expected to have a much greater specificity for HTLV infected individuals with essentially the same sensitivity currently exhibited by tests using the p21E recombinant protein.

A final embodiment might include both the 2B3A and 3A3B peptides. Truly HTLV infected individuals would react with 2B3A and possibly the 3A3B peptides. Individuals who are not infected with HTLV-I or HTLV-II but who possess antibodies which cross react with the p21E recombinant protein, and so may be positive on HTLV screening assays, will react only with the 3A3B protein. This embodiment would have the advantage of providing an antigen which will give a positive signal for both the truly HTLV infected individuals and the uninfected, HTLV indeterminate individuals. This allows for a more precise determination of a given individual's seroreactivity.

V. HTLV-Peptide Vaccine Compositions

Also included in the invention is a vaccine composition containing the 2B3A peptide immunogenic peptide carrier to which the peptide is bound. More specifically, the vaccine contains a peptide having an HTLV-specific antigenic region consisting essentially of the amino acid sequence identified by SEQ ID NO: 22, in combination with a an immunogenic peptide carrier.

Particularly useful immunogenic carriers for the peptide (s) include keyhole limpet hemocyanin (KLH), tetanus toxoid, poly-1-(Lys:Glu), peanut agglutinin, poly-D-lysine, diphtheria toxoid, ovalbumin, soybean agglutinin, bovine serum albumin (BSA), human serum albumin, and the like.

The 2B3A peptide may be conjugated to the carrier by a variety of known methods, including chemical derivatization and by genetic engineering techniques. Such latter technique is disclosed in more detail by Gerald Quinnan, "Proceedings of a Workshop," Nov. 13–14, 1984. Vaccines and inocula of the present invention may be administered by injection, usually intramuscularly or subcutaneously, orally by means of an enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the mammal to be immunized, the carrier when used, the adjuvant when used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide.

In any event, the immunogen contained in a vaccine or an inoculum is present in an "effective amount," which amount depends upon a variety of factors as is well known in the immunological arts, e.g., the body weight of the mammal to be immunized, the carrier moiety used, the adjuvant used, the duration of protection sought, and the desired immunization protocol.

VI. Anti-2B3A Peptide Antibodies

This section describes the preparation of human monoclonal antibodies (Mabs) specific against the 2B3A peptide, the preparation of human recombinant antibodies (Rabs) specific against the 2B3A peptide, and uses of the antibodies as a passive vaccine against HTLV-I viral infection.

A. Preparation of Human Anti-2B3A Mabs

Hybridomas which produce anti-2B3A antibodies can be generated by fusing an anti-2B3A antibody-producing lymphocyte isolated from B lymphocytes from an HTLV-I or HTLV-II infected human, with a fusion partner myeloma cell, using hybridoma production techniques known in the art (Harlow).

In one exemplary method of hybridoma production, B-lymphocytes isolated from the peripheral blood of an asymptomatic HTLV-I infected individual are activated with Epstein-Barr virus (EBV), and subsequently selected for antibodies which are immunoreactive with the 2B3A peptides, as described in Example 1B.

Culture of cells showing positive anti-2B3A activity are expanded and fused with a suitable human or mouse-human myeloma fusion partner, such as the GLI-H7 myeloma partner cells described in the Materials section below, using polyethylene glycol (PEG) as a fusogen. Hybridomas are then selected by growth in a medium containing hypoxanthine, aminopterin, thymidine and ouabain, according to well-established criteria (Mitchell).

Supernatants of hybridoma cultures are tested for presence of immunoglobulins which are immunoreactive with the 2B3A peptide, for example using methods described in Example 2.

Positive hybridoma cultures identified by the above steps are subcloned by limiting dilution and re-tested for immunoreactivity with the 2B3A peptide. Positive subclones are expanded and are further tested for immunoglobulin isotype and for 2B3A peptide immunoreactivity.

B. Preparation of Human Recombinant Anti-2B3A Antibodies

Cultures of hybridomas which produce anti-2B3A Mabs are prepared as above. Messenger RNA (mRNA) is isolated from the cells, and the mRNA is used to produce corresponding cDNA's according to well-known methods (Maniatis).

The coding sequences for the light-chain and heavy-chain variable regions of the immunoglobulin genes are amplified by PCR methods employing known PCR primers for heavy and light chain IgG variable regions (Larrick, 1989, 1991, 1992). The amplified coding sequence fragment for the light-chain variable region is purified, cut between appropriate restriction enzymes, and inserted into a suitable expression vector for expression of IgG light chain, following published procedures (Larrick, 1989, 1991, 1992). The construction of one suitable expression vector, identified herein as pSXRD.kappa-IgG is given in Example 3.

The amplified coding sequence fragment for the heavy-chain variable region is similarly purified, cut appropriate restriction enzymes, and inserted into a suitable expression vector for expression of IgG heavy chain, following published procedures (Larrick, 1989, 1991). One suitable expression vector for expressing the heavy-chain variable region is the pcDNA1/neo.IgG1 vector. The vector can be constructed by modifying a pcDNA1 vector (Invitrogen, San Diego, Calif.)) by addition of a IgG heavy-chain constant coding region (Larrick, 1992).

The two plasmids are then cotransfected into either CHO or GLI-H7 cells using lipofection or electroporation. Selection for the heavy plasmid was carried out using antibiotic GENETICIN™ (G418, BRL #860-1811I). Cells are assayed for IgG production and subcloned. The subclones are assayed for binding to the 2B3A peptide. Positive clones were subcloned several times to guarantee purity.

Alternatively, a clone selection method, such as has been described (Huse, McCafferty) may be used to generate recombinant anti-2B3A antibodies, employing as a source of B lymphocyte variable-region coding regions, cDNAs prepared from B lymphocytes isolated from a human infected with HTLV-I or HTLV-II.

The cDNA's are inserted into phage vectors, the vectors are expressed in a suitable *E. coli* bacterial host, and the released phage are selected by affinity binding to a solid support containing the antigen. The captured phage are then used to reinfect a bacterial host.

C. Passive Vaccine Compositions

The human anti-2B3A Mabs or Rabs prepared as above are employed in a vaccine composition for use in the treatment and/or prophylaxis of HTLV-I and/or HTLV-II infection. In this approach Mabs or Rabs which recognize the 2B3A peptide are administered to individuals who may have been exposed to and/or infected with HTLV-I or HTLV-II. Binding of these antibodies to HTLV-I infected cells then provides a humoral immune response in which macrophages destroy B lymphocytes having bound anti HTLV-I antibodies.

The anti-HTLV-I antibodies are formulated in a suitable solution for injection, typically by parenteral route, to form the vaccine composition. The composition is administered in an amount effective to block HTLV infection, in an uninfected individual, or to inhibit viral replication in an infected patient. Preferred antibody dosage is in the range between about 0.5 to 5 mg antibody/kg body weight. The composition may be administered at spaced intervals, preferably about 1 to 4 week intervals, for treatment of an infected individual. Vaccination may be prior to an expected infection, or in treating existing HTLV-I infection.

In one general application, infants whose mothers are diagnosed as having HTLV-I are injected with the antibody composition, to prevent development of the viral infection, particularly when the infant is breast fed over an extended period. The antibodies may be administered parenterally, e.g., intramuscularly, subcutaneously, or intravenously, or in the case of infants, also by oral administration, in a method for treating or preventing HTLV-I by immune prophylaxis.

VII. Identification of 3A3B Crossreactive Protein(s)

The identification of HTLV epitope 3A3B which is specifically crossreactive with HTLV-noninfected humans can be used, according to procedures described in this section, for identifying the protein(s) which are responsible for inducing the cross-reactive antibody.

A. Antibody Identification of Protein

Polyclonal or monoclonal antibodies specific against the 3A3B peptide may be employed to isolate and identify cross-reactive peptides present in the serum of cross-reactive individuals, i.e., individuals who are negative for the presence of HTLV virus, but whose serum is cross-reactive with the HTLV p21E antigen.

The anti-3A3B antibody may be a polyclonal or monoclonal antibody made according to conventional techniques, using the 3A3B peptide as antigen (Harlow). The peptide antigen is preferably conjugated to a suitable carrier protein, such as keyhole limpet hemocyanin, and injected into a suitable animal, such as a rabbit, for generating polyclonal antibodies, or a mouse, or producing Mabs.

Alternatively, the antibody may be purified by affinity purification by attaching the 3A3B peptide to a solid support, and capturing antibodies from cross-reactive individuals, employing known affinity purification methods (Harlow).

To isolate the cross-reactive protein from a cross-reactive individual, anti-3A3B antibody from above is attached to a solid support, by standard derivatization methods, and a sample of plasma or whole cell lysate isolated from the 3A3B crossreactive individual is passed over the support bed, to entrap cross-reactive proteins on the support. The trapped proteins can be released from the column, candidate proteins can be purified by preparative SDS-PAGE or Chromatography, and the purified proteins can be sequenced using standard methods.

Once a partial protein sequence is obtained, it is possible to identify the coding sequence responsible for the peptide using methods well known to the art (Maniatis et al., SISPA patent). One such method would involve isolating nucleic acids from a serum and/or PBMC sample from a 3A3B crossreactive individual followed by construction of a λgt10 library. The resulting library would be probed with labeled degenerate primers to identify clones containing hybridizing sequences in the serum which may encode the isolated 3A3B cross-reactive protein. Other methodologies, which are beyond the scope of this application may also be employed.

The following examples illustrate various aspects of the invention, but are in no way intended to limit the scope thereof.

MATERIALS

The materials used in the following examples were as follows:

Enzymes: DNAase I and alkaline phosphatase were obtained by Boehringer Mannheim Biochemicals (BMB, Indianapolis, Ind.); EcoRI, EcoRI methylase, DNA ligase, and Polymerase I, from New England Biolabs (NEB, Beverly, Mass.); and RNase was obtained from Sigma (St. Louis, Mo.).

Other reagents: EcoRI linkers were obtained from NEB; and nitro blue tetrazolium (NBT), 5-bromo-4-chloro-3-indolyl phosphate (BCIP), 5-bromo-4-chloro-3-indolyl-β-D-galactopyranoside (X-gal) and isopropyl β-D-thiogalactopyranoside (IPTG) were obtained from Sigma.

The GLI-H7 cell line is a human-mouse heteromyeloma fusion partner cell line, constructed from fusion of a mouse NS-1 myeloma with a human activated B lymphocyte, as described by Carroll. The HEp-2 cell line is an epidermoid carcinoma (from human larynx) cell line, obtained from the American Type Culture Collection (ATCC), Rockville, Md. (ATCC-CCL-23). Chinese Hamster Ovary cells (DUX-B11) were obtained from L. A. Chasin (Urlaub).

Cell culture media (PFHM, RPMI, IMDM) were obtained from Gibco Laboratories.

EXAMPLE 1

Preparation of 2B3A and 3A3B Recombinant Peptides

A. Constructing Expression Vectors

A plasmid containing a full-copy DNA insert derived from the HTLV-I genome was obtained from Drs. R. C. Gallo and F. Wong-Staal of the Laboratory of Tumor Cell Biology, National Institutes of Health (Bethesda, Md.).

The gp21 coding region (FIG. 2) was derived from the gp21 coding region present in the HTLV-I clone sp65 MT-2 obtained from Dr. Wong-Stahl. Oligonucleotide primers designed to amplify selected portions of HTLV-I gp21 (FIG. 3) were synthesized on an automated synthesizer (Applied Biosystems, Foster City, Calif.), following manufacturers instructions. All of the primers contained either a BamHI, NcoI and/or EcoR I site located at their 5' ends to facilitate cloning of the amplified DNAs as in-frame insertion into the pGEX-GLI expression system.

PCR was performed according the manufacturer's instructions (Perkin-Elmer/Cetus, Norwalk, Conn.) and all PCR reactions contained 2 ng of the HTLV-I clone sp65 MT2 (generously provided by Dr. F. Wong-Staal) as template and 1.0 μM of the appropriate oligonucleotide primers. PCR amplification was carried out for 25 cycles of template denaturation (1 minute at 94° C.), primer annealing (2 minutes at 50° C.), and primer extension (2 minutes at 72° C.). Amplified DNAs were purified, digested for 2 hours with the appropriate restriction enzymes and ligated into the expression vector pGEX-GLI, which is a modified version of the commercially available vector pGEX-2 (Pharmacia, Piscataway, N.J.), which had previously digested with the same restriction enzymes.

B. Preparing Antibodies for Screening

Peripheral B cells were isolated from an asymptomatic HTLV-I infected individual and activated with Epstein-Barr virus (EBV) at $10^4$ cells per well in a 96 well microtiter plate as previously described (Perkins; Foung). After 2 days in culture specific anti-HTLV-I IgG activity was assessed using an HTLV-I viral lysate-based enzyme immunoassay (Diagnostic Biotechnology, Singapore). Anti HTLV-I activity was detected, and the EMB immortalized B cells were then grown in culture for about 1 month during which time the spent supernatants from the cultures were saved. Subsequent Western blot analysis using a HTLV-I confirmatory assay (Diagnostic Biotechnology) determined that 3 of the EBV activated B cell lines, designated 3E9, 5G4, and 6E9, reacted strongly with the recombinant env protein p21E. The supernatants were then diluted 1/2 in BLOTTO and used to screen the isolated gp21 recombinant proteins. Upon subsequent fusion to mouse-human heteromyeloma cells, none of these 3 EBV activated B cell lines were successfully fused and the antibody production of the EBV activated B cells eventually ceased. However, the activated B cell supernatants did provide a highly specific antibody preparation which was useful in the screening procedure described below. In addition, the isolation of antibodies to the 2B3A from 3 separate EBV activated B cells confirms that antibodies to the 2B3A peptide antigen are a major component of the immune response of infected individuals to HTLV-I or HTLV-II.

C. Screening Immunogenic Peptides

Plasmid containing bacteria were screened for protein production by Western blot analysis of crude lysates prepared from 2 ml cultures of the transformed *E. coli*. One-tenth volume of the whole cell lysate was loaded per lane and was electrophoresed on a 12.0% polyacrylamide SDS gel (Laemmli). The resulting gel was electroblotted onto nitrocellulose filter paper (Schleicher and Schuell, Keene, N.H.) and the HTLV-I Western blots were incubated overnight at room temperature with EBV activated B cell tissue culture supernatants diluted 1/2 (Example 1B), or HTLV-infected or control antisera diluted 1/100. All sera and supernatants were diluted into BLOTTO (10 mM TRIS-HCl, pH 7.4, 5% nonfat dry milk, 2.5% normal goat sera, and 0.5% Tween-20). The Western blots were washed 3 times with TTBS wash buffer (10 mM TRIS-HCl pH 7.4, 150 mM NaCl, 0.05% Tween-20) for 5 minutes each.

Bound human IgG was detected by a 1 hour incubation with goat-anti-human IgG conjugated to alkaline phosphatase (Promega, Madison, Wis.) for 1 hour. This was followed by 4,5 minute rinses with TTBS. Bound second antibody was detected by incubating the strips in a substrate solution containing 5-bromo-4-chloro 3-indolyphosphate (BCIP) and Nitroblue tetrazolium (NBT) in 100 mM TRIS-HCl, pH 9.5, and 50 mM MgCl2. The resulting Western blots were screened with sera from HTLV-I infected or uninfected individuals. The results of these analyses are presented in Table 1.

The recombinant clones 2A3B, 2A2B, 2B3A, and 3A3B were all DNA sequenced by the dideoxy termination procedure (Maniatis et al.). The sequence of the DNA inserts obtained was consistent with the DNA sequences of the primers and templates used in their construction, and would allow for the production of the desired recombinant proteins.

D. Purification of Recombinant Antigens

Purification of recombinant fusion protein was performed essentially as described (20). Briefly, a 10 ml overnight culture of bacteria containing the recombinant plasmid of interest was diluted 1/100 into flasks containing 500 mls NZYDT media (Maniatis, et al.) with 100 μg/ml ampicillin. Expression of fusion protein was induced by the addition of IPTG (final concentration 0.2 mM) to log-phase cultures. The cultures were grown for an addition 3 to 4 hours at 37° C. at which point the bacteria were pelleted by centrifugation at 5000 x g for 10 minutes. The cells were resuspended in 20 mls cold MTBS and were lysed by several cycles of freezing and thawing. After lysis proteins were solubilized by the addition of Triton-X100 (Sigma, St. Louis, Mo.) to 1.0%, DNAse I to 1 μg/ml, and Aprotinin to 1.0%. After incubation for 5 minutes at 25° C., insoluble cellular debris was pelleted by centrifugation 2 times at 10,000 x g for 10 minutes and the supernatants were reserved. Aliquots from both the pellet and supernatant fraction were analyzed by SDS-PAGE (Laemmli) to determine if the recombinant proteins were solubilized by the above procedure.

The 2A3B, 2A2B, and 3A3B recombinant proteins were all present in the soluble fraction. For all 3 of the recombinant proteins a 1 liter culture resulted in the purification of 1–2 mgs of fusion protein at a purity of approximately 50%. The supernatants were then passed through a column containing 0.8 ml of glutathione agarose (Pharmacia, Piscataway, N.J.), which was pre-treated as recommended by the manufacturer. The column was washed with 10 mls of MTBS plus 1% Triton and 1% Apoprotnin followed by a 5 ml wash with MTBS alone. Bound proteins were eluted with buffer containing 5 mM glutathione in 50 mM Tris pH 8.0 and 10, 1 ml fractions were collected. The location of the peak of eluted protein was determined by measuring the absorbance at 280 nm of the fractions and by SDS-PAGE analysis of aliquots of the fractions. Fractions containing significant amounts of protein were pooled and aliquots of this pool were frozen at −70° C. for subsequent analysis.

EXAMPLE 2

Serological Paneling of the Purified p21E Recombinants vs. HTLV-I, HTLV-II and p21E Indeterminate Sera A. Antisera The antisera used in these analyses included a well-characterized panel of sera from 26 HTLV-I, and 28 HTLV-II infected individuals (Lipka et al. 1991; Hadlock et al. 1992). All of the HTLV-I and HTLV-II sera had antibody profiles meeting standard criteria for HTLV infection (antibodies to p24 gag and gp46 and/or gp68 env proteins). In addition, the sera were typed as being HTLV-I infected both by virtue of their positive reactivity towards the recombinant HTLV-I antigen MTA1 and/or through PCR using HTLV-I specific oligonucleotide primers and probes (Lipka, et al. 1992b). Similarly, the 32 HTLV-II infected individuals were identified by their reactivity towards the recombinant HTLV-II antigen K55 and/or by PCR using HTLV-II specific primers and probes (Lipka et al. 1992b).

The gp21 peptide antigens were also tested for their immunoreactivity with sera from 7 HTLV-I negative individuals and sera from 18 individuals whose sera were reactive with the p21E recombinant protein but who were negative for the presence of HTLV nucleic acids when tested by PCR using HTLV-I and HTLV-I specific primers and probes. In addition these 18 p21E reactive sera did not meet serological criteria for being HTLV infected. The HTLV-I and HTLV-I infected individuals were all from the Northern California area, with the exception of antisera J103 which was from a HTLV-I infected Japanese blood donor. The uninfected sera were all derived from blood donors to the Stanford University Blood Bank. The 18 p21E reactive-HTLV negative sera were either from blood donors from the Northern California area or were provided by the Center for Disease Control, Atlanta, Ga.

B. Seroreactivity of Purified Recombinant Peptides

The recombinant proteins 2A2B, 2B3A, and 3A3B were prepared as in Example 1. Aliquots of the purified proteins were separated under reducing conditions on a 11.5% polyacrylamide gel (Laemmli). The resolved proteins were electroblotted onto a nitrocellulose membrane, blocked with BLOTTO, air dried, and cut into 3 mm wide strips.

In the assay, the test strips from above were first rehydrated in TTBS buffer, and the strips were incubated overnight with human test sera, diluted 1:50 in BLOTTO. The strips were washed several times with wash buffer, then incubated for one hour with goat anti-human IgG conjugated to alkaline phosphatase (Bio-Rad, Hercules, Calif.). After washing, color development was achieved by incubating the strips in a substrate solution containing NBT and BCIP in 100 mM Tris-HCl buffer, pH 9.5, 50 mM $MgCl_2$. Color development was continued until a uniform background developed on the strip and was halted by rinsing the strips two times with de-ionized water. The recombinant proteins 2A2B, 2B3A, and 3A3B were tested against the panels of HTLV infected and negative sera described in example 2A. The results of the immunoassays are given in Table 2 above.

EXAMPLE 3

Construction of pSXRD.kappa-Ig

Construction of the mammalian expression vector pSXRD.kappa-Ig was performed in several steps. The base vector is pUC18. Into the BamHI site of pUC18 was inserted the 585 bp BamHI-BGlII fragment from the HBV surface antigen gene comprising the polyadenylation signal (Larrick, et al., 1992). The orientation was such that the BamHI site of the HBV insert was nearest to the EcoRI site of the vector. The region between the HindIII and HincII sites of the polylinker were removed by digesting the plasmid with those two enzymes and then blunting the HindIII site using the Klenow fragment of DNA polymerase. After ligation, the resultant plasmid was designated pUCHBV3'. A unique SalI site was inserted into the BamHI site using a synthetic oligonucleotide primer.

Between the unique EcoRI site and the SalI site were inserted the following fragments in a series of ligations: (a) An SV40 Early promoter, bounded by an EcoRI site (created by the addition of a synthetic oligonucleotide into the PvuII site immediately preceding the SV40 promoter and the HindIII site immediately preceding the T antigen initiation codon, (b) a stuffer fragment derived from an irrelevant cDNA bounded by a HindIII site and ending in an XbaI site, (c) an XbaI-Bg1II fragment from pcDNA1/neo containing the SV40 polyadenylation signal and the RSV promoter. The XbaI site is provided in the vector and the Bg1II site was inserted using PCR cloning to be situated at the junction between the RSV promoter and the Neo selectable marker, and (d) the murine DHRF cDNA, bounded by a Bg1II site at the 3' end. The restriction sites were inserted using PCR.

While the invention has been described with reference to particular embodiments, methods of construction, and uses, it will be clear to those in the are that various other uses, formulations, and methods of practice are within the contemplation of the present invention.

It is claimed:

1. A peptide antigen, consisting of an amino acid sequence identified by SEQ ID NO: 1.

2. The peptide antigen of claim 1, wherein the amino acid sequence is identified by SEQ ID NO: 22.

3. The peptide antigen of claim 1, wherein the amino acid sequence is identified by SEQ ID NO: 29.

4. A kit for detecting the presence of HTLV-I or HTLV-II infection in a human serum sample, comprising (a) a solid support;

(b) attached to the solid support, in a reaction zone, a peptide antigen consisting of an amino acid sequence identified by SEQ ID NO: 1; and (c) reporter means for detecting the presence of human antibodies bound to said support.

5. The kit of claim 4, wherein the amino acid sequence is identified by SEQ ID NO: 22.

6. The kit of claim 4, wherein the amino acid sequence is identified by SEQ ID NO: 29.

7. The kit of claim 4, which further includes a second reaction zone on the solid support, and attached to this second reaction zone, a second peptide antigen consisting of an amino acid sequence identified by SEQ ID NO: 2.

8. The kit of claim 4, which further includes a second reaction zone on the solid support, and attached to this second reaction zone, a second peptide antigen capable of discriminating between serum antibodies specific against HTLV-I and HTLV-II.

9. The kit of claim 8, wherein the second peptide antigen consists of the amino acid sequence identified by SEQ ID NO: 3.

10. The kit of claim 8, wherein the second peptide antigen consists of the amino acid sequence identified by SEQ ID NO: 4.

11. A kit for detecting the presence of HTLV-I or HTLV-II infection in a human serum, comprising (a) a solid support having first and second, and third reaction zones, (b) immobilized at said first reaction zone, a first peptide antigen consisting of the amino acid sequence identified by SEQ ID NO: 1;

(c) immobilized at said second reaction zone, a second peptide antigen consisting of the amino acid sequence identified by SEQ ID NO: 2;

(d) immobilized at said third reaction zone, a third peptide antigen capable of discriminating between serum antibodies specific against HTLV-I or HTLV-II; and (e) reporter means for detecting the presence of human antibodies bound to said support.

12. The kit of claim 11, wherein said first peptide antigen consists of the amino acid sequence identified by SEQ ID NO: 22, and said second peptide antigen consists of the amino acid sequence identified by SEQ ID NO: 30.

13. The kit of claim 11, wherein said third peptide antigen consists of the amino acid sequence identified by SEQ ID NO: 3.

14. The kit of claim 11, wherein said third peptide antigen consists of the amino acid sequence identified by SEQ ID NO: 4.

15. A method of identifying HTLV-I or HTLV-II infection in a human subject, comprising reacting serum from the subject with a peptide antigen consisting of the amino acid sequence identified by SEQ ID NO: 1, and determining the presence of peptide-antibody complexes as an indication of the presence of HTLV-I or HTLV-II antibodies in the serum.

16. The method of claim 15, wherein the peptide antigen consists of the amino acid sequence identified by SEQ ID NO: 22.

17. The method of claim 15, wherein the peptide antigen consists of the amino acid sequence identified by SEQ ID NO: 29.

* * * * *

UNITED STATES PATENT AND TRADEMARK OFFICE

CERTIFICATE OF CORRECTION

PATENT NO : 5,643,714

DATED : July 1, 1997

INVENTOR(S) : Kenneth G. Hadlock et al.

It is certified that error appears in the above-identified patent and that said Letters Patent are hereby corrected as shown below:

Column 1, line 13, insert --This invention was made with Government support under contracts AI22557 and HL33811 awarded by the National Institutes of Health. The Government has certain rights in this invention.--

Signed and Sealed this

Twenty-seventh Day of April, 1999

Attest:

Q. TODD DICKINSON

Attesting Officer

*Acting Commissioner of Patents and Trademarks*

UNITED STATES PATENT AND TRADEMARK OFFICE

CERTIFICATE OF CORRECTION

PATENT NO. : 5,643,714
DATED : July 1, 1997
INVENTOR(S) : Kenneth G. Hadlock et al.

It is certified that error appears in the above-identified patent and that said Letters Patent is hereby corrected as shown below:

Column 1,
Line 13, insert --this invention was made with Government support under contracts AI22557 and HL33811 awwarded by the National Institutes of Health. The Government has certain rights in this invention.--

Signed and Sealed this

Fourteenth Day of August, 2001

Attest:

Nicholas P. Godici

Attesting Officer

NICHOLAS P. GODICI
*Acting Director of the United States Patent and Trademark Office*